(12) United States Patent
Chen

(10) Patent No.: US 6,432,989 B1
(45) Date of Patent: Aug. 13, 2002

(54) USE OF CRF ANTAGONISTS TO TREAT CIRCADIAN RHYTHM DISORDERS

(75) Inventor: Yuhpyng L. Chen, Waterford, CT (US)

(73) Assignee: Pfizer Inc, New York, NY (US)

(*) Notice: Subject to any disclaimer, the term of this patent is extended or adjusted under 35 U.S.C. 154(b) by 0 days.

(21) Appl. No.: 09/587,007

(22) Filed: Jun. 5, 2000

Related U.S. Application Data

(60) Provisional application No. 60/151,183, filed on Aug. 27, 1999.

(51) Int. Cl.⁷ .................................................. A61K 31/44
(52) U.S. Cl. ........................................................ 514/348
(58) Field of Search .......................................... 514/348

(56) References Cited

U.S. PATENT DOCUMENTS

| | | | |
|---|---|---|---|
| 4,605,642 A | 8/1986 | Rivier et al. | |
| 5,063,245 A | 11/1991 | Abreu et al. | |
| 5,880,135 A | 3/1999 | Gully et al. | |
| 5,962,479 A | * 10/1999 | Chen .......................... | 514/348 |

FOREIGN PATENT DOCUMENTS

| | | |
|---|---|---|
| EP | 576350 | 6/1993 |
| EP | 773023 | 5/1997 |
| EP | 0778277 | 6/1997 |
| WO | 9413676 | 6/1994 |
| WO | 9413677 | 6/1994 |
| WO | 9510506 | 4/1995 |
| WO | 9533727 | 12/1995 |
| WO | 9533750 | 12/1995 |
| WO | 9534563 | 12/1995 |
| WO | 9635689 | 11/1996 |
| WO | 9639400 | 12/1996 |
| WO | 9700868 | 1/1997 |
| WO | 9714684 | 4/1997 |
| WO | 9729109 | 8/1997 |
| WO | 9729110 | 8/1997 |
| WO | 9735580 | 10/1997 |
| WO | 9735846 | 10/1997 |
| WO | 9744038 | 11/1997 |
| WO | 9803510 | 1/1998 |
| WO | 9805661 | 2/1998 |
| WO | 9808821 | 3/1998 |
| WO | 9808846 | 3/1998 |
| WO | 9808847 | 3/1998 |
| WO | 9811075 | 3/1998 |
| WO | 9815543 | 4/1998 |
| WO | 9821200 | 5/1998 |
| WO | 9827066 | 6/1998 |
| WO | 9829397 | 7/1998 |
| WO | 9829413 | 7/1998 |
| WO | 9835967 | 8/1998 |
| WO | 9842699 | 10/1998 |
| WO | 9845295 | 10/1998 |
| WO | 9847874 | 10/1998 |
| WO | 9847903 | 10/1998 |
| WO | 9900373 | 1/1999 |
| WO | 9901439 | 1/1999 |
| WO | 9901454 | 1/1999 |
| WO | 9910350 | 3/1999 |
| WO | 9912908 | 3/1999 |
| WO | 9938868 | 8/1999 |

OTHER PUBLICATIONS

Seifritz et al, Chemical Abstracts, vol. 129, abstract No. 198249, 1998.*
Graf et al, Embase Abstracts, abstract No. 1988240282, 1988.*
Search Report: EP 00 30 7074 Jul. 24, 2001.

* cited by examiner

Primary Examiner—William R. A. Jarvis
(74) Attorney, Agent, or Firm—Peter C. Richardson; Paul H. Ginsburg; Seth H. Jacobs

(57) ABSTRACT

A corticotropin releasing factor (CRF) antagonist is administered to treat disorders that can be treated by altering circadian rhythm.

4 Claims, No Drawings

USE OF CRF ANTAGONISTS TO TREAT CIRCADIAN RHYTHM DISORDERS

This application claims priority under 35 U.S.C. §119(e) from U.S. application Ser. No. 60/151,183 filed Aug. 27, 1999, which application is hereby incorporated by reference herein.

FIELD OF THE INVENTION

This invention relates to the use of CRF antagonists in the treatment of certain conditions, and related compositions.

BACKGROUND OF THE INVENTION

CRF antagonists are disclosed in U.S. Pat. Nos. 4,605,642 (Issued Aug. 12, 1986) and 5,063,245 (issued Nov. 5, 1991). They are also disclosed in International patent publications WO 95/33750 (published Dec. 14, 1995); WO 95/34563 (published Dec. 21, 1995); WO 94/13676 (published Jun. 23, 1994); WO 94/13677 (published Jun. 23, 1994); WO 95/33727 (published Dec. 14, 1995); WO 98/05661 (published Feb. 12, 1998); WO 98/08847 (published Mar. 5, 1998); and WO 98/08846 (published Mar. 5, 1998) and European patent publications EP 778277 (published Jun. 11, 1997) and EP 773023 (published May 14, 1997). CRF antagonists are also disclosed in the following patent publications: EP 576350; WO 95/10506 (published Apr. 20, 1995); WO 96/35689 (published Nov. 14, 1996); WO 96/39400 (published Dec. 12, 1996); WO 97/00868 (published Jan. 9, 1997); WO 97/14684 (published Apr. 24, 1997); WO 97/29109 (published Aug. 14, 1997); WO 97/29110 (published Aug. 14, 1997); WO 97/35580 (published Oct. 2, 1997); WO 97/35846 (published Oct. 2, 1997), WO 97/44038 (published Nov.27, 1997); WO 98/03510 (published Jan. 29, 1998); WO 98/08821 (published Mar. 5, 1998); WO 98/11075 (published Mar. 19, 1998), WO 98/15543 (published Apr. 16, 1998); WO 98/21200 (published May 22, 1998); WO 98/27066 (published Jun. 25, 1998); WO 98/29397 (published Jul. 9, 1998); WO 98/29413 (published Jul. 9, 1998); WO 98/42699 (published Oct. 1, 1998); WO 98/35967 (published Aug. 20, 1998); WO 98/45295 (published Oct. 15, 1998); WO 98/47874 (published Oct. 29, 1998); WO 98/47903 (published Oct. 29, 1998); WO 99/01454 (published Jan. 14, 1999); WO 99/01439 (published Jan. 14, 1999); WO 99/10350 (published Mar. 4, 1999); WO 99/12908 (published Mar. 18, 1999); WO 99/00373 (published Jan. 7, 1999); and WO 99/38868 (published Aug. 5, 1999).

The importance of CRF antagonists is set out in the literature, e.g., P. Black, Scientific American SCIENCE & MEDICINE,1995, p. 16–25; T. Lovenberg, et al., Current Pharmaceutical Design, 1995, 1: 305–316; and U.S. Pat. No. 5,063,245. An outline of the activities possessed by CRF antagonists is found in M. J. Owens et al., 1991, Pharm. Rev., 43:425–473. CRF antagonists are described in the art as being effective in the treatment of stress-related illnesses, mood disorders such as depression, major depressive disorder, single episode depression, recurrent depression, child abuse induced depression, postpartum depression, dysthemia, bipolar disorders, and cyclothymia; chronic fatigue syndrome; eating disorders such as anorexia and bulimia nervosa; generalized anxiety disorder; panic disorder; phobias, obsessive-compulsive disorder; post-traumatic stress disorder; pain perception such as fibromyalgia; headache; gastrointestinal diseases; hemorrhagic stress; ulcers; stress-induced psychotic episodes; fever; diarrhea; post-operative ileus; colonic hypersensitivity, irritable bowel syndrome; Crohn's disease; spastic colon; inflammatory disorders such as rheumatoid arthritis and osteoarthritis; pain; asthma; psoriasis; allergies; osteoporosis; premature birth; hypertension, congestive heart failure; sleep disorders; neurodegenerative diseases such as Alzheimer's disease, senile dementia of the Alzheimer's type, multiinfarct dementia, Parkinson's disease, and Huntington's disease; head trauma; ischemic neuronal damage; excitotoxic neuronal damage; epilepsy; stroke; spinal cord trauma; psychosocial dwarfism; euthyroid sick syndrome; syndrome of inappropriate antidiarrhetic hormone; obesity; chemical dependencies and addictions; drug and alcohol withdrawal symptoms; infertility; cancer; muscular spasms; urinary incontinence; hypoglycemia and immune dysfunctions including stress induced immune dysfunctions, immune suppression and human immunodeficiency virus infections; and stress-induced infections in humans and animals.

SUMMARY OF THE INVENTION

The present invention relates to a method of treating a condition comprising administering a corticotropin releasing factor (CRF) antagonist in an amount effective to treat the condition, the condition being selected from the group consisting of:

a) disorders that can be treated by altering circadian rhythm; and b) depression, further wherein a second compound for treating depression is administered, the second compound for treating depression having an onset of action that is delayed with respect to that of the CRF antagonist.

In another aspect, the present invention relates to a method for treating or preventing a cardiovascular disease that involves administering a CRF antagonist in combination with a non-CRF antagonist compound for treating the disease. The invention also relates to treatment of migraine or non-migraine headache by administration of a CRF antagonist in combination with a non-CRF antagonist compound that treats such condition and to treatment of emesis using a CRF antagonist in combination with a non-CRF antagonist compound for treating emesis.

DETAILED DESCRIPTION OF THE INVENTION

All patents, patent publications, and literature references cited herein are hereby incorporated by reference.

In one aspect, the present invention provides for treatment of disorders that can be treated by altering circadian rhythm, e.g., abnormal circadian rhythm, by administration of a CRF antagonist. Abnormal circadian rhythm treated according to the invention can be associated with several types of disorders, including, without limitation, time zone change syndrome, seasonal affective disorder, irregular sleep-wake pattern, delayed sleep phase syndrome, advanced sleep phase syndrome, non-24 hour sleep wake disorder, light-induced clock resetting, REM sleep disorder, hypersomnia, parasomnia, narcolepsy, nocturnal enuresis, restless legs syndrome, sleep apnea, dysthymia, and abnormal circadian rhythm associated with chronic administration and withdrawal of antidepressant agents.

If desired, a second compound, e.g., a non-CRF antagonist that is useful for treating sleep disorder, can be administered before, with, or after, administration of the CRF antagonist. Any such second compound useful for treating sleep disorder may be employed, including but not limited to tachykinin antagonists, melatoninergic agonists, such as melatonin, GABA brain receptor agonists, serotonin receptor (such as 5HT1b, 5HT2c, 5HT7) antagonists, inverse agonists, agonists and other compounds. Specific compounds for treatment of sleep disorder include melatonin, carpipramine, and doxylamine. These and other compounds are described, for example, in U.S. Pat. Nos. 5,908,932; 5,902,813; 5,883,094; 5,874,450; 5,849,781; 5,856,529; and U.S. Pat. No. 4,956,362.

It is intended that reference to particular compounds herein be interpreted to mean that the pharmaceutically acceptable salts and prodrugs of those compounds, may also be employed. Such reference is also intended to be interpreted that modified CRF antagonists may also be employed. For example, the invention encompasses use of a CRF antagonist linked to a non-CRF antagonist to form a prodrug which hydrolyzes upon administration to form active components.

The invention also encompasses treatment of depression with a CRF antagonist and with a second compound having delayed action for treating depression. According to this aspect of the invention, the CRF antagonist initiates treatment of the depression with a quick-acting effect, which treatment is supplemented by the delayed effect of the second compound.

Compounds for treating depression that have a delayed effect include, without limitation, compounds that are selective serotonin reuptake inhibitors (SSRIs), tricyclic antidepressants, norepinephrine reuptake inhibitors, noradrenaline reuptake inhibitors, lithium, α2-adrenoreceptor agonists, $5HT_{1A}$ inhibitors, and monoamine oxidase type A inhibitors. Examples include bupropion, sertraline, fluoxetine, trazodone, citalopram, fluvoxamine, paroxetine, venlafaxine, roboxetine, imipramine, amitriptyline, trimipramine, doxepin, desipramine, nortriptyline, protriptyline, amoxapine, clomipramine, maprotiline, brofaromine, milnacipran, and buspirone. It understood by those skilled in this art that compounds administered for treatment of depression may have other beneficial effects, such as ameliorating sleep disturbance or sexual dysfunction. Compounds having a delayed effect for treating depression also include the combination of an SSRI and $5HT_2$ antagonist (such as risperidone) administered, for example, to patients who do not respond to SSRI therapy alone. Administration of these delayed-action compounds for treating depression is carried out using well-known dosages and formulations.

Any CRF antagonist can be used to practice the invention, including those that are described in U.S. Pat. Nos. 4,605,642 and 5,063,245; International patent publications WO 95/33750; WO 95/34563; WO 94/13676; WO 94/13677; WO 95/33727; WO 98/05661; WO 98108847; and WO 98108846; and European patent publications EP 778277; and EP 773023. They also include those of the following patent publications: EP 576350; WO 95/10506; WO 96/35689; WO 96139400; WO 97/00868; WO 97/14684; WO 97/29109; WO 97/29110; WO 97/35580; WO 97/35846; WO 97/44038; WO 98/03510; WO 98/08821; WO 98/11075; WO 98/15543; WO 98/21200; WO 98/27066; WO 98/29397; WO 98/29413; WO 98/42699; WO 98/35967; WO 98/45295; WO 98/47874, WO 98/47903, WO 99/01454, WO 99/01439, WO 99/10350; WO 99/12908; WO 99/00373, and WO 99/38868. As noted above, the texts of all of these publications are incorporated by reference herein in their entireties.

Following are listed particular examples of CRF antagonists that may be used in practicing the invention. It is understood that in the generic formulae employed below, the variables employed, e.g., "A", "B", "$R_1$", "$R_2$", etc. have the meanings attributed to them only in the particular Roman numeral section in which they are found. Thus, the meaning attributed, for example, to "$R^1$" is different for the structures in section I and the structures of the other sections.

I. For example, the CRF antagonist may be of the following formula, described in WO 94/13677:

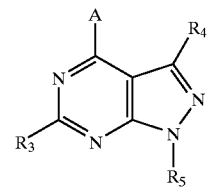

and the pharmaceutically acceptable acid addition salts thereof, wherein

A is $NR_1R_2$, $CR_1R_2R_{11}$, or $C(=CR_1R_{12})R_2$, $NHCR_1R_2R_{11}$, $OCR_1R_2R_{11}$, $SCR_1R_2R_{11}$, $NHNR_1R_2$, $CR_2R_{11}NHR_1$, $CR_2R_{11}OR_1$, $CR_2R_{11}SR_1$ or $C(O)R_2$;

$R_1$ is hydrogen, or $C_1$–$C_6$ alkyl which may be substituted by one or two substituents $R_6$ independenty selected from the group consisting of hydroxy, fluoro, chloro, bromo, iodo, $C_1$–$C_6$ alkoxy, O—C(O)—($C_1$–$C_6$ alkyl), O—C(O)—N($C_1$–$C_4$ alkyl)($C_1$–$C_2$ alkyl); amino, NH($C_1$–$C_4$ alkyl), S($C_1$–$C_6$ alkyl), OC(O)NH($C_1$–$C_4$ alkyl), N($C_1$–$C_2$ alkyl)C(O)($C_1$–$C_4$ alkyl), NHC(O) ($C_1$–$C_4$ alkyl), COOH, CO($C_1$–$C_4$ alkyl), C(O)NH ($C_1$–$C_4$ alkyl), C(O)N($C_1$–$C_4$ alkyl)($C_1$–$C_2$ alkyl), SH, CN, $NO_2$, SO($C_1$–$C_4$ alkyl); $SO_2$($C_1$–$C_4$ alkyl), $SO_2$NH($C_1$–$C_4$ alkyl), $SO_2$N($C_1$–$C_4$ alkyl)($C_1$–$C_2$ alkyl), and said $C_1$–$C_6$ alkyl may have one or two double or triple bonds;

$R^2$ is $C_1$–$C_{12}$ alkyl, aryl or ($C_1$–$C_{10}$ alkylene)aryl wherein said aryl is phenyl, naphthyl, thienyl, benzothienyl, pyridyl, quinolyl, pyrazinolyl, pyrimidyl, imidazolyl, furanyl, benzofuranyl, benzothiazolyl, isothiazolyl, benzisothiazolyl, thiazolyl, isoxazolyl, benzisoxazolyl, benzimidazolyl, triazolyl, pyrazolyl, pyrrolyl, indolyl, azaindolyl, oxazolyl, or benzoxazolyl; 3- to 8-membered cycloalkyl or ($C_1$–$C_6$ alkylene) cycloalkyl, wherein said cycloalkyl may have one or two of O, S or N—Z, wherein Z is hydrogen, substituted, independently, for one or two carbons of said cycloalkyl, $C_1$–$C_4$ alkyl, benzyl or $C_1$–$C_4$ alkanoyl, wherein $R^2$ may be substituted independently by from one to three of chloro, fluoro, or $C_1$–$C_4$ alkyl, or one of hydroxy, bromo, iodo, $C_1$–$C_6$ alkoxy, OC(O) ($C_1$–$C_6$ alkyl), O—C—N($C_1$–$C_4$ alkyl)($C_1$–$C_2$ alkyl), S($C_1$–$C_6$ alkyl), $NH_2$, NH($C_1$–$C_2$ alkyl), N($C_1$–$C_4$ alkyl) C(O)($C_1$–$C_4$ alkyl), NHC(O)($C_1$–$C_4$ alkyl), COOH, C(O)O($C_1$–$C_4$ alkyl), C(O)NH($C_1$–$C_4$ alkyl), C(O)N($C_1$–$C_4$ alkyl)($C_1$–$C_2$ alkyl), SH, CN, $NO_2$, SO($C_1$–$C_4$ alkyl), $SO_2$($C_1$–$C_4$ alkyl), $SO_2$NH($C_1$–$C_4$ alkyl), $SO_2$N($C_1$–$C_4$ alkyl)($C_1$–$C_2$ alkyl), and wherein said $C_1$–$C_{12}$ alkyl or $C_1$–$C_{10}$ alkylene may have one to three double or triple bonds; or $NR_1R_2$ or $CR_1R_2R_{11}$, may form a 4- to 8-membered ring optionally having one or two double bonds or one or two of O, S or N—Z wherein Z is hydrogen, $C_1$–$C_4$ alkyl, benzyl, or $C_1$–$C_4$ alkanoyl;

$R_3$ is hydrogen, $C_1$–$C_6$ alkyl, fluoro, chloro, bromo, iodo, hydroxy, amino, O($C_1$–$C_6$ alkyl), NH($C_1$–$C_8$ alkyl), N($C_1$–$C_4$ alkyl)($C_1$–$C_2$ alkyl), SH, S($C_1$–$C_4$ alkyl), SO($C_1$–$C_4$ alkyl), or SO$_2$($C_1$–$C_4$ alkyl), wherein said $C_1$–$C_4$ alkyl and $C_1$–$C_6$ alkyl may have one or two double or triple bonds and may be substituted by from 1 to 3 $R_7$ substituents independently selected from the group consisting of hydroxy, amino, $C_1$–$C_3$ alkoxy, dimethylamino, diethylamino, methylamino, ethylamino, NHC(O)CH$_3$, fluoro, chloro or $C_1$–$C_3$ thioalkyl;

$R_4$ is hydrogen, $C_1$–$C_6$ alkyl, fluoro, chloro, bromo, iodo, $C_1$–$C_6$ alkoxy, amino, NH($C_1$–$C_6$ alkyl), N($C_1$–$C_6$ alkyl) ($C_1$–$C_2$ alkyl), SO$_n$($C_1$–$C_6$ alkyl), wherein n is 0, 1 or 2, cyano, hydroxy, carboxy, or amido, wherein said $C_1$–$C_6$ alkyls may be substituted by one to three of hydroxy, amino, carboxy, amido, NHC(O)($C_1$–$C_4$ alkyl), NH($C_1$–$C_4$ alkyl), N($C_1$–$C_4$ alkyl)($C_1$–$C_2$ alkyl), C(O)O($C_1$–$C_4$ alkyl), $C_1$–$C_3$ alkoxy, $C_1$–$C_3$ thioalkyl, fluoro, bromo, chloro, iodo, cyano or nitro;

$R_5$ is phenyl, naphthyl, thienyl, benzothienyl, pyridyl, quinolyl, pyrazinolyl, pyrimidyl, imidazolyl, furanyl, benzofuranyl, benzothiazolyl, isothiazolyl, benzoisothiazolyl, thiazolyl, isoxazolyl, benzisoxazolyl, benzimidazolyl, triazolyl, pyrazolyl, pyrrolyl, indolyl, pyrrolopyridyl benzoxazolyl, oxazolyl, pyrrolidinyl, thiazolidinyl, piperazinyl, piperidinyl, or tetrazolyl, wherein each one of the above groups may be substituted independently by from one to three of fluoro, chloro, bromo, formyl, $C_1$–$C_6$ alkyl, $C_1$–$C_6$ alkoxy or trifluoromethyt, or one of hydroxy, iodo, cyano, nitro, amino, cyclopropyl, NH($C_1$–$C_4$ alkyl), N($C_1$–$C_4$ alkyl)($C_1$–$C_2$ alkyl), COO ($C_1$–$C_4$ alkyl), CO($C_1$–$C_4$ alkyl), SO$_2$NH($C_1$–$C_4$ alkyl), SO$_2$N($C_1$–$C_4$ alkyl)($C_1$–$C_2$ alkyl), SO$_2$NH$_2$, NHSO$_2$($C_1$–$C_4$ alkyl), S($C_1$–$C_6$ alkyl), SO$_2$($C_1$–$C_6$ alkyl), wherein said $C_1$–$C_4$ alkyl and $C_1$–$C_6$ alkyl may have one double or triple bond and may be substituted by one or two of fluoro, chloro, hydroxy, amino, methylamino, dimethylamino or acetyl; with the proviso that $R_5$ is not unsubstituted phenyl; and $R_{11}$ is hydrogen, hydroxy, fluoro, chloro, COO($C_1$–$C_2$ alkyl), cyano, or CO($C_1$–$C_2$ alkyl); and $R_{12}$ is hydrogen or $C_1$–$C_4$ alkyl;

(a) A is not straight chain $C_1$–$C_{12}$ alkyl;

(b) when $R_3$ is hydrogen, A is benzyl or phenethyl, and $R_4$ is fluoro, chloro, bromo or iodo, then $R_5$ is not 5'-deoxy-ribofuranosyl or 5'-amino-5'-deoxy-ribofuranosyl; and (c) when $R^5$ is phenyl, said phenyl is substituted by two or three substituents.

II. The invention also relates to use of a CRF antagonist of the following formula, described in WO 94/13676:

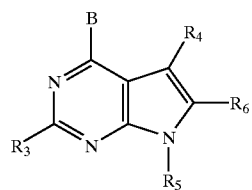

and the acid addition salts thereof, wherein

B is XA wherein X is (CH$_2$)$_n$ in which n is 0, 1 or 2, NH, 0, S, N($C_1$–$C_4$ alkyl);

A is NR$_1$R$_2$, CR$_1$R$_2$R$_{11}$, or C(=CR$_2$R$_{12}$)R$_1$;

$R_1$ is hydrogen, or $C_1$–$C_6$ alkyl which may be substituted by one or two substituents $R_7$ independently selected from the group consisting of hydroxy, fluoro, chloro, bromo, iodo, $C_1$–$C_8$ alkoxy, O—C(=O)—($C_1$–$C_{10}$ alkyl), O—C(=O)NH($C_1$–$C_4$ alkyl), OC(=O)N ($C_1$–$C_4$ alkyl)($C_1$–$C_2$ alkyl), amino, NH($C_1$–$C_4$ alkyl), N($C_1$–$C_2$ alkyl)($C_1$–$C_4$ alkyl), S($C_1$–$C_6$ alkyl), N($C_1$–$C_4$alkyl)C(=O)($C_1$–$C_4$ alkyl), NH($C_1$–$C_4$ alkyl), COOH, C(=O)O($C_1$–$C_4$ alkyl), C(=O)NH ($C_1$–$C_4$ alkyl), C(=O)N($C_1$–$C_4$ alkyl)($C_1$–$C_2$ alkyl), SH, CN, NO$_2$, SO($C_1$–$C_4$ alkyl), SO$_2$($C_1$–$C_4$ alkyl), SO$_2$NH($C_1$–$C_4$ alkyl), SO$_2$N($C_1$–$C_4$ alkyl)($C_1$–$C_2$ alkyl), and said $C_1$–$C_6$ alkyl may contain one or two double or triple bonds;

$R_2$ is $C_1$–$C_{12}$ alkyl, aryl or ($C_1$–$C_{10}$ alkylene)aryl wherein said aryl is phenyl, naphthyl, thienyl, benzothienyl, pyridyl, quinolyl, pyrazinyl, pyrimidyl, imidazolyl, furanyl, benzofuranyl, benzothiazolyl, isothiazolyl, benzisothiazolyl, thiazolyl, isoxazolyl, benzisoxazolyl, benzimidazolyl, triazolyl, pyrazolyl, pyrrolyl, indolyl, pyrrolopyridyl, oxazolyl, or benzoxazolyl; 3- to 8-membered cycloalkyl or ($C_1$–$C_6$ alkylene) cycloalkyl, wherein said cycloalkyl may contain benzimidazolyl, triazolyl, pyrazolyl, pyrrolyl, indolyl, pyrrolopyridyl, oxazolyl, or benzoxazolyl; 3-to 8-membered cycloalkyl or ($C_1$–$C_6$ alkylene) cycloaklyl, wherein said cycloalkyl may cantain one or two of O, S or N—Z wherein Z is hydrogen, $C_1$–$C_4$ alkyl, benzyl or $C_1$–$C_4$ alkanoyl, wherein $R_2$ may be substituted independently by from one to three of chloro, fluoro, or $C_1$–$C_4$ alkyl, or one of hydroxy, bromo, iodo, $C_1$–$C_6$ alkoxy, O—C(=O)($C_1$–$C_4$ alkyl), O—C—N($C_1$–$C_4$ alkyl)($C_1$–$C_2$ alkyl), NHC(=O) ($C_1$–$C_4$), COOH, C(=O)O($C_1$–$C_4$ alkyl), C(=O)NH ($C_1$–$C_4$ alkyl), C(=O)N($C_1$–$C_4$ alkyl)($C_1$–$C_2$ alkyl), SH, CN, NO$_2$, SO($C_1$–$C_4$ alkyl), SO$_2$($C_1$–$C_4$ alkyl), SO$_2$NH($C_1$–$C_4$ SO$_2$N($C_1$–$C_4$ alkyl)($C_1$–$C_2$ alkyl), and wherein said $C_1$–$C_2$ alkyl or $C_1$–$C_{10}$ alkyl may contain one to three double or triple bonds; or when A is NR$_1$R$_2$ or CR$_1$R$_2$R$_1$R$_{11}$, then R$_1$ and R$_2$ taken together with the atom to which they are attached may form a saturated 4- to 8-membered optionally containing one or two double bonds or one or two of O, S or N—Z wherein Z is hydrogen, $C_1$–$C_4$ alkyl, or $C_1$–$C_4$ alkanoyl;

$R_3$ is hydrogen, $C_1$–$C_6$ alkyl, fluoro, chloro, bromo, iodo, hydroxy, amino, O($C_1$–$C_6$ alkyl), NH($C_1$–$C_6$ alkyl), N($C_1$–$C_4$ alkyl)($C_1$–$C_2$ alkyl), SH, S($C_1$–$C_4$ alkyl), SO($C_1$–$C_4$ alkyl), or SO$_2$($C_1$–$C_4$ alkyl), wherein said $C_1$–$C_4$ alkyl and $C_1$–$C_6$ alkyl may contain from one or two double or triple bonds and may be substituted by from 1 to 3 substituents $R_8$ independently selected from the group consisting of hydroxy, amino, $C_1$–$C_3$ alkoxy, dimethylamino, diethylamino, methylamino, ethylamino, NHCH$_3$, fluoro, chloro or $C_1$–$C_3$ thioalkyl;

$R_4$ and $R_6$ are each independently hydrogen, $C_1$–$C_6$ alkyl, fluoro, chloro, bromo, iodo, $C_1$–$C_6$ alkoxy, amino, NH($C_1$–$C_6$ alkyl), N($C_1$–$C_6$ alkyl)($C_1$–$C_2$ alkyl), SO$_n$ ($C_1$–$C_6$ alkyl), wherein n is 0, 1 or 2, cyano, hydroxy, carboxy, or amido, wherein said $C_1$–$C_6$ alkyls may be substituted by one to three of hydroxy, amino, carboxy, amido, NHC(=O)($C_1$–$C_4$ alkyl), NH($C_1$–$C_4$ alkyl), N($C_{1-C4}$ alkyl)($C_1$–$C_2$ alkyl), C(=O)O($C_1$–$C_4$ alkyl), $C_1$–$C_3$ alkoxy, $C_1$–$C_3$ thioalkyl, fluoro, bromo, chloro, iodo, cyano or nitro;

$R_5$ is phenyl, naphthyl, thienyl, benzothienyl, pyridyl, quinolyl, pyrazinyl, pyrimidyl, imidazolyl, furanyl, benzofuranyl, benzothiazolyl, isothiazolyl, benzisothiazolyl, thiazolyl, isoxazolyl, benzisoxazolyl, benzimidazolyl, triazolyl, pyrazolyl, pyrrolyl, indolyl, azaindolyl, benzoxazolyl, oxazolyl, pyrrolidinyl, thiazolidinyl, morpholinyl, piperidinyl, piperazinyl, tetrazolyl, or 3- to 8-membered cycloalkyl or 9- to 12-membered bicycloalkyl, optionally containing one to three of O, S or N—Z wherein Z is hydrogen, $C_1$–$C_4$ alkyl, $C_1$–$C_4$ alkanoyl, phenyl or phenylmethyl, wherein each one of the above groups may be substituted independently by from one to four of fluoro, chloro, $C_1$–$C_6$ alkyl, $C_1$–$C_6$ alkoxy or trifluoromethyl, or one of bromo, iodo, cyano, nitro, amino, NH($C_1$–$C_4$ alkyl), N($C_1$–$C_4$)($C_1$–$C_2$ alkyl), COO($C_1$–$C_4$ alkyl), CO($C_1$–$C_4$ alkyl), $SO_2$NH($C_1$–$C_4$ alkyl), $SO_2$N($C_1$–$C_4$ alkyl)($C_1$–$C_2$ alkyl), $SO_2NH_2$, $NHSO_2$($C_1$–$C_4$ alkyl), S($C_1$–$C_6$ alkyl), $SO_2$($C_1$–$C_6$ alkyl), wherein said $C_1$–$C_4$ alkyl and $C_1$–$C_6$ alkyl may be substituted by one or two of fluoro, chloro, hydroxy, amino, methylamino, dimethylamino or acetyl; with the proviso that $R_5$ is not unsubstituted phenyl;

$R_{11}$, is hydrogen, hydroxy, fluoro, chloro, COO($C_1$–$C_2$ alkyl), cyano, or CO($C_1$–$C_2$ alkyl); and $R_{12}$ is hydrogen or $C_1$–$C_4$ alkyl; with the proviso that (1) when $R_5$ is 4-bromophenyl, $R_3$ is hydrogen, and $R_4$ and $R_6$ are methyl, then B is not methylamino or ethyl, and (2) when $R_5$ is 4-bromophenyl, and $R_3$, $R_4$ and $R_6$ are methyl, then B is not 2-hydroxyethylamino.

III. It is also possible to employ a CRF antagonist that has a structure selected from the group shown below, and pharmaceutically acceptable salts and esters thereof, as described in WO 95/33750:

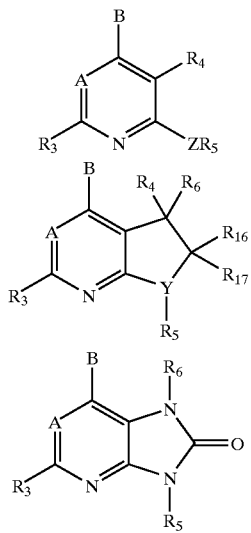

wherein
A is $CR_7$ or N;
B is $NR_1R_2$, $CR_1R_2R_{11}$, $C(=CR_2R_{12})R_1$, $NHCHR_1R_2$, $OCHR_1R_2$, $SCHR_1R_2$, $CHR_2OR_{12}$, $CHR_2SR_{12}$, C(S) $R_2$ or $C(O)R_2$;
Y is CH or N;
Z is NH, O, S, N ($C_1$–$C_2$ alkyl), or $CR_{13}R_{14}$, wherein $R_{13}$ and $R_{14}$ are each independently hydrogen, trifluoromethyl, or $C_1C_4$ alkyl, or one of $R_{13}$ and $R_{14}$ may be cyano, chloro, bromo, iodo, fluoro, hydroxy, O($C_1$–$C_2$ alkyl), amino, NH($C_1C_2$ alkyl), or $CR_{13}R_{14}$ may be C=O or cyclopropyl;
$R_1$ is $C_1$–$C_6$ alkyl which may be substituted by one or two substituents $R_4$ independently selected from the group consisting of hydroxy, fluoro, chloro, bromo, iodo, $C_1$–$C_4$ alkoxy, O—CO—($C_1$–$C_4$ alkyl), O—CO—NH ($C_1$–$C_4$ alkyl), O—CO—N($C_1$–$C_4$ alkyl)($C_1$–$C_2$ alkyl), NH($C_1$–$C_4$ alkyl), N($C_1$–$C_2$ alkyl)(C–$C_4$ alkyl), S($C_1$–$C_4$ alkyl), N($C_1$–$C_4$alkyl)CO($C_1$–$C_4$ alkyl), NHCO($C_1$–$C_4$ alkyl), COO($C_1$–$C_4$ alkyl), CONH ($C_1$–$C_4$ alkyl), CON($C_1$–$C_4$ alkyl)($C_1$–$C_2$ alkyl), S($C_1$–$C_4$ alkyl), CN, $NO_2$, SO($C_1$–$C_4$ alkyl), $SO_2$ ($C_1$–$C_4$ alkyl), and said $C_1$–$C_6$ alkyl or $C_1$–$C_4$ alkyl may contain one double or triple bond;

$R_2$ is $C_1$–$C_{12}$ alkyl, aryl or ($C_1$–$C_4$ alkylene)aryl wherein said aryl is phenyl, naphthyl, thienyl, benzothienyl, pyridyl, quinolyl, pyrazinyl, pyrimidyl, imidazolyl, furanyl, benzofuranyl, benzothiazolyl, isothiazolyl, benzisothiazolyl, benzisoxazolyl, benzimidazolyl, indolyl, or benzoxazolyl; 3- to 8-membered cycloalkyl or ($C_1$–$C_6$ alkylene)cycloalkyl, wherein said cycloalkyl may contain one or two of O, S or N-$R_9$ wherein $R_9$ is hydrogen, or $C_1$–$C_4$ alkyl, wherein the above defined $R_2$ may be substituted independently by from one to three of chloro, fluoro, or $C_1$–$C_4$ alkyl, or one of bromo, iodo, $C_1$–$C_4$ alkoxy, O—CO—($C_1$–$C_6$ alkyl), O—CO—N($C_1$–$C_4$ alkyl)($C_1$–$C_2$ alkyl), S($C_1$–$C_6$ alkyl), CN, $NO_2$, SO($C_1$–$C_4$ alkyl), or $SO_2$($C_1$–$C_4$ alkyl), and wherein said $C_1$–$C_{12}$ alkyl or $C_1$–$C_4$ alkylene may contain one double or triple bond; or $NR_1R_2$ or $CR_1R_2R_{11}$, may form a saturated 5- to 8-membered carbocyclic ring which may contain one or two double bonds or one or two of O or S;

$R_3$ is methyl, ethyl, fluoro, chloro, bromo, iodo, cyano, methoxy, $OCF_3$, methylthio, methylsulfonyl, $CH_2OH$ or $CH_2OCH_3$;

$R_4$ is hydrogen, $C_1$–$C_4$ alkyl, fluoro, chloro, bromo, iodo, $C_1$–$C_4$ alkoxy, amino, nitro, NH($C_1$–$C_4$ alkyl), N($C_1$–$C_4$ alkyl)($C_1$–$C_2$ alkyl), $SO_n$($C_1$–$C_4$ alkyl), wherein n is 0, 1 or 2, cyano, hydroxy, CO($C_1$–$C_4$ alkyl), CHO, or COO($C_1$–$C_4$ alkyl), wherein said $C_1$–$C_4$ alkyl may contain one or two double or triple bonds and may be substituted by one or two of hydroxy, amino, carboxy, $NHCOCH_3$, NH($C_1$–$C_2$ alkyl), N($C_1$–$C_2$ alkyl)$_2$, COO($C_1$–$C_4$ alkyl), CO($C_1$–$C_4$ alkyl), $C_1$–$C_3$ alkoxy, $C_1$–$C_3$ thioalkyl, fluoro, chloro, cyano or nitro;

$R_5$ is phenyl, naphthyl, thienyl, benzothienyl, pyridyl, quinolyl, pyrazinyl, pyrimidyl, furanyl, benzofuranyl, benzothiazolyl, or indolyl, wherein each one of the above groups $R_5$ is substituted independently by from one to three of fluoro, chloro, $C_1$–$C_6$ alkyl, or $C_1$–$C_6$ alkoxy, or one of hydroxy, iodo, bromo, formyl, cyano, nitro, trifluoromethyl, amino, NH($C_1$–$C_4$ alkyl), N($C_1$–$C_6$)($C_1$–$C_2$ alkyl), COOH, COO($C_1$–$C_4$ alkyl), CO($C_1$–$C_4$ alkyl), $SO_2$NH($C_1$–$C_4$ alkyl), $SO_2$N ($C_1$–$C_4$alkyl)($C_1$–$C_2$ alkyl), $SO_2NH_2$, $NHSO_2$($C_1$–$C_4$ alkyl), S($C_1$–$C_6$ alkyl), or $SO_2$($C_1$–$C_6$ alkyl), wherein said $C_1$–$C_4$ alkyl and $C_1$–$C_6$ alkyl may be substituted by one or two of fluoro, hydroxy, amino, methylamino, dimethylamino or acetyl;

$R_6$ is hydrogen, or $C_1$–$C_6$ alkyl, wherein said $C_1$–$C_6$ alkyl may be substituted by one hydroxy, methoxy, ethoxy or fluoro;

$R_7$ is hydrogen, $C_1$–$C_4$ alkyl, fluoro, chloro, bromo, iodo, cyano, hydroxy, O($C_1$–$C_4$ alkyl), C(O)($C_1$–$C_4$ alkyl), or C(O)O($C_1$–$C_4$ alkyl), wherein the $C_1$–$C_4$ alkyl groups may be substituted with one hydroxy, chloro or bromo, or one to three fluoro;

$R_{11}$ is hydrogen, hydroxy, fluoro, or methoxy;

$R_{12}$ is hydrogen or $C_1$–$C_4$ alkyl; and $R_{16}$ and $R_{17}$ are each independently hydrogen, hydroxy, methyl, ethyl, methoxy, or ethoxy, except that they are not both methoxy or ethoxy, and $CR_4R_6$ and $CR_{16}R_{17}$ each independently may be C=O.

IV. It also possible to employ a CRF antagonist of the following formula, disclosed in WO 95/34563:

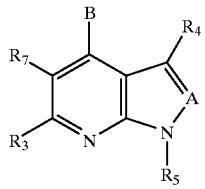

and the pharmaceutically acceptable acid addition salts thereof, wherein

A is N or —$CR_6$;

B is —$NR_1R_2$, —$CR_1R_2R_{11}$, —$C(=CR_2R_{12})R_1$, —$NHCHR_1R_2$, —$OCHR_1R_2$, —$SCHR_1R_2$, —$CHR_2OR_{12}$, —$CHR_2SR_{12}$, —C(S)$R_1$ or —C(O)$R_1$;

$R_1$ is $C_1$–$C_6$ alkyl which may optionally be substituted with one or two substituents independently selected from the group consisting of hydroxy, fluoro, chloro, bromo, iodo, $C_1$–$C_4$ alkoxy, —O—CO—($C_1$–$C_4$ alkyl), —O—CO—NH($C_1$–$C_4$ alkyl), —O—CO—N($C_1$–$C_4$ alkyl)($C_1$–$C_2$ alkyl), —N($C_1$–$C_2$ alkyl)($C_1$–$C_4$ alkyl), —S($C_1$–$C_4$ alkyl), —N($C_1$–$C_4$ alkyl)CO($C_1$–$C_4$ alkyl), —NHCO($C_1$–$C_4$ alkyl), —COO($C_1$–$C_4$ alkyl), —CONH($C_1$–$C_4$ alkyl), —CON($C_1$–$C_4$ alkyl)($C_1$–$C_2$ alkyl), CN, $NO_2$, —$SO_2$($C_1$–$C_4$ alkyl), and wherein any of the foregoing $C_1$–$C_4$ alkyl and $C_1$–$C_6$ $R_2$ is $C_1$–$C_{12}$ alkyl, aryl, —($C_1$–$C_4$ alkylene)aryl wherein said aryl is phenyl, naphthyl, thienyl, benzothienyl, pyridyl, quinolyl, pyrazinyl, pyrimidyl, imidazolyl, furanyl, benzofuranyl, benzothiazolyl, isothiazolyl, benzisothiazolyl, thiazolyl, isoxazolyl, benzisoxazolyl, benzimidazolyl, triazolyl, pyrazolyl, pyrrolyl, indolyl, oxazolyl, or benzoxazolyl; or 3- to 8-membered cycloalkyl or —($C_1$–$C_6$ alkylene)cycloalkyl, wherein one or two of the ring carbons of said cycloalkyl having at least 4 ring members and the cycloalkyl moiety of said —($C_1$–$C_6$ alkylene)cycloalkyl having at least 4 ring members may optionally be replaced by an oxygen or sulfur atom or by N—Z wherein Z is hydrogen; or $C_1$–$C_4$ alkyl, and wherein each of said groups $R_2$ may optionally be substituted with from one to three substituents independently selected from chloro, fluoro, and $C_1$–$C_4$ alkyl, or by one substituent selected from bromo, iodo, $C_1$–$C_6$ alkoxy, —O—CO—($C_1$–$C_6$ alkyl), —S($C_1$–$C_6$ alkyl), —COO($C_1$–$C_4$ alkyl), CN, $NO_2$, —SO($C_1$–$C_4$ alkyl), and —$SO_2$($C_1$–$C_4$ alkyl), and wherein said $C_1$–$C_{12}$ alkyl and the $C_1$–$C_4$ alkylene moiety of said —($C_1$–$C_4$ alkylene)aryl may optionally contain one carbon-carbon double or triple bond;

or —$NR_1R_2$ may form a saturated 5 to 8-membered heterocyclic ring, or —$CHR_1R_2$ may form a saturated 5 to 8-membered carbocyclic ring, wherein each of these rings may optionally contain one or two carbon-carbon double bonds and wherein one or two of the carbon atoms of each of these rings may optionally be replaced with a sulfur or oxygen atom;

$R_3$ is $C_1$–$C_4$ alkyl, fluoro, chloro, bromo, iodo, —$CH_2OH$, —$CH_2OCH_3$, —O($C_1$–$C_3$ alkyl), —S($C_1$–$C_3$ alkyl), or —$SO_2$($C_1$–$C_3$ alkyl), wherein said $C_1$–$C_3$ alkyl may optionally contain one carbon-carbon double or triple bond;

$R_4$ is hydrogen, $C_1$–$C_6$ alkyl, fluoro, chloro, bromo, iodo, $C_1$–$C_4$ alkoxy, amino, —$NHCH_3$, —$N(CH_3)_2$, —$CH_2OH$, —$CH_2OCH_3$, or —$SO_n$($C_1$–$C_4$ alkyl), wherein n is 0, 1 or 2, cyano, hydroxy, —CO($C_1$–$C_4$ alkyl), —CHO, or —COO($C_1$–$C_4$ alkyl) wherein the $C_1$–$C_4$ alkyl moieties in the foregoing $R_4$ groups may optionally contain one carbon-carbon double or triple bond;

$R_5$ is phenyl, naphthyl, thienyl, benzothienyl, pyridyl, pyrimidyl, benzofuranyl, pyrazinyl or benzothiazolyl, wherein each one of said groups $R_5$ may optionally be substituted with from one to three substituents independently selected from fluoro, chloro, $C_1$–$C_6$ alkyl and $C_1$–$C_6$ alkoxy, or by one substituent selected from iodo, hydroxy, bromo, formyl, cyano, nitro, amino, trifluoromethyl, —NH ($C_1$–$C_4$ alkyl), —N($C_1$–$C_6$)($C_1$–$C_2$ alkyl), —COO($C_1$–$C_4$ alkyl), —CO($C_1$–$C_4$ alkyl), —COOH, —$SO_2$NH ($C_1$–$C_4$alkyl), —$SO_2$N($C_1$–$C_4$ alkyl)($C_1$–$C_2$ alkyl), —$SO_2NH_2$, —$NHSO_2$($C_1$–$C_4$ alkyl), —S($C_1C_6$ alkyl) and —$SO_2$($C_1C_6$ alkyl), wherein each of said $C_1$–$C_4$ alkyl and $C_1$–$C_6$ alkyl moieties in the foregoing $R^5$ groups may optionally be substituted with one to three fluorine atoms;

$R_6$ is hydrogen, $C_1$–$C_4$ alkyl, fluoro, chloro, bromo, iodo, —$CH_2OH$, —$CH_2OCH_3$, or $C_1$–$C_4$ alkoxy;

$R_7$ is hydrogen, $C_1$–$C_4$ alkyl, fluoro, chloro, bromo, iodo, —O($C_1$–$C_4$ alkyl), cyano, —$CH_2OH$, —$CH_2O$($C_1$–$C_2$ alkyl), —CO($C_1$–$C_2$ alkyl), or —COO($C_1$–$C_2$ alkyl);

$R_{11}$ is hydrogen, hydroxy, fluoro, or methoxy; and $R_{12}$ is hydrogen or $C_1$–$C_4$ alkyl;

with the proviso that when A is N, then: (a) B is not unsubstituted alkyl; (b) $R_5$ is not unsubstituted phenyl or monosubstituted phenyl; and (c) $R_3$ is not unsubstituted alkyl;

or a pharmaceutically acceptable salt of such compound.

V. In another embodiment, the CRF antagonist is of the following formula, disclosed in EP 778277:

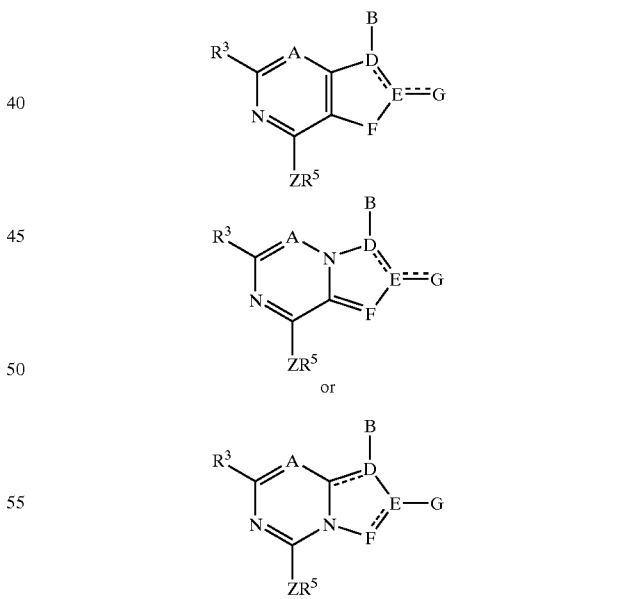

or a pharmaceutically acceptable salt thereof, wherein the dashed lines represent optional double bonds;

A is nitrogen or $CR^7$;

B is —$NR^1R^2$, —$CR^1R^2R^{10}$, —$C(=CR^2R^{11})R^1$, —$NHCR^1R^2R^{10}$, —$OCR^1R^2R^{10}$, —$SCR^1R^2R^{10}$, —$CR^2R^{10}NHR^1$—$CR^2R^{10}OR^1$—$CR^2R^{10}SR^1$ or —$COR^2$;

D is nitrogen and is single bonded to all atoms to which it is attached, or D is carbon and is either double bonded to E in formulas I and II or double bonded to the adjacent carbon atom common to both fused rings in formula III, or D is CH and is single bonded to E in formulas I and II;

E is nitrogen, CH or carbon;

F is oxygen, sulfur, $CHR^4$ or $NR^4$ when it is single bonded to E and F is nitrogen or $CR^4$ when it is double bonded to E;

G, when single bonded to E, is hydrogen, $C_1$–$C_4$ alkyl, —S($C_1$–$C_4$ alkyl), —O($C_1$–$C_4$ alkyl), $NH_2$, —NH($C_1$–$C_4$ alkyl) or —N($C_1$–$C_2$ alkyl)($C_1$–$C_4$ alkyl), wherein each of the $C_1$–$C_4$ alkyl groups of G may optionally be substituted with one hydroxy, —O($C_1$–$C_2$ alkyl) or fluoro group; G, when double bonded to E, is oxygen, sulfur or NH; and G, when E is nitrogen and double bonded to D or F, is absent;

$R^1$ is hydrogen, $C_1$–$C_6$ alkyl optionally substituted with one or two substituents $R^8$ independently selected from hydroxy, fluoro, chloro, bromo, iodo, $C_1$–$C_4$ alkoxy, $CF_3$, —C(=O)O—($C_1$–$C_4$)alkyl, —OC(=O)($C_1$–$C_4$ alkyl), —OC(=O)N($C_1$–$C_4$ alkyl)($C_1$–$C_2$ alkyl), —NHCO($C_1$–$C_4$ alkyl), —COOH, —COO($C_1$–$C_4$ alkyl), —CONH($C_1$–$C_4$ alkyl), —CON($C_1$–$C_4$ alkyl)($C_1$–$C_2$ alkyl), —S($C_1$–$C_4$ alkyl), —CN, —$NO_2$, —SO($C_1$–$C_4$ alkyl), —$SO_2$($C_1$–$C_4$ alkyl), —$SO_2$NH($C_1$–$C_4$ alkyl) and —$SO_2$N($C_1$–$C_4$ alkyl)($C_1$–$C_2$ alkyl), wherein each of the $C_1$–$C_4$ alkyl groups in the foregoing $R^1$ groups may optionally contain one or two double or triple bonds;

$R^2$ is $C_1$–$C_{12}$ alkyl which may optionally contain from one to three double or triple bonds, aryl or ($C_1$–$C_4$ alkylene)aryl, wherein said aryl and the aryl moiety of said ($C_1$–$C_4$ alkylene)aryl is selected from phenyl, naphthyl, thienyl, benzothienyl, pyridyl, quinolyl, pyrazinyl, pyrimidinyl, imidazolyl, furanyl, benzofuranyl, benzothiazolyl, isothiazolyl, pyrazolyl, pyrrolyl, indolyl, pyrrolopyridyl, oxazolyl and benzoxazolyl; $C_3$–$C_8$ cycloalkyl or ($C_1$–$C_6$ alkylene)($C_3$–$C_8$ cycloalkyl), wherein one or two of the carbon atoms of said cycloalkyl and the 5 to 8 membered cycloalkyl moieties of said ($C_1$–$C_6$ alkylene)($C_3$–$C_8$ cycloalkyl) may optionally and independently be replaced by an oxygen or sulfur atom or by $NZ^2$ wherein $Z^2$ is selected from hydrogen, $C^1$–$C_4$ alkyl, benzyl and $C_1$–$C_4$ alkanoyl, and wherein each of the foregoing $R^2$ groups may optionally be substituted with from one to three substituents independently selected from chloro, fluoro, hydroxy and $C_1$–$C_4$ alkyl, or with one substituent selected from bromo, iodo, $C_1$–$C_6$ alkoxy, —OC(=O)($C_1$–$C_6$ alkyl), —OC(=O)N($C_1$–$C_4$ alkyl)($C_1$–$C_2$ alkyl), —S($C_1$–$C_6$ alkyl), amino, —NH($C_1$–$C_2$ alkyl), —N($C_1$–$C_2$ alkyl)($C_1$–$C_4$ alkyl), —N($C_1$–$C_4$ alkyl)-CO—($C_1$–$C_4$ alkyl), —NHCO($C_1$–$C_4$ alkyl), —COOH, —COO($C_1$–$C_4$ alkyl), —CONH($C_1$–$C_4$ alkyl), —CON($C_1$–$C_4$ alkyl)($C_1$–$C_2$ alkyl), —SH, —CN, —$NO_2$, —SO($C_1$–$C_4$ alkyl), —$SO_2$($C_1$–$C_4$ alkyl), —$SO_2$NH($C_1$–$C_4$ alkyl) and —$SO_2$N($C_1$–$C_4$ alkyl)($C_1$–$C_2$ alkyl);

—$NR^1R^2$ or $CR^1R^2R^{10}$ may form a saturated 3 to 8 membered carbocyclic ring which may optionally contain from one to three double bonds and wherein one or two of the ring carbon atoms of such 5 to 8 membered rings may optionally and independenty be replaced by an oxygen or sulfur atom or by $NZ^3$ wherein $Z^3$ is hydrogen, $C_1$–$C_4$ alkyl, benzyl or $C_1$–$C_4$ alkanoyl;

$R^3$ is hydrogen, $C_1$–$C_4$ alkyl, —O($C_1$–$C_4$ alkyl), chloro, fluoro, bromo, iodo, —CN, —S($C_1$–$C_4$ alkyl) or —$SO_2$($C_1$–$C_4$ alkyl) wherein each of the ($C_1$–$C_4$ alkyl) moieties in the foregoing $R^3$ groups may optionally be substituted with one substituent $R^9$ selected from hydroxy, fluoro and ($C_1$–$C_2$ alkoxy);

each $R^4$ is, independently, hydrogen, ($C_1$–$C_6$ alkyl), fluoro, chloro, bromo, iodo, hydroxy, cyano, amino, nitro, —O($C_1$–$C_4$ alkyl), —N($C_1$–$C_4$ alkyl)($C_1$–$C_2$ alkyl), —S($C_1$–$C_4$ alkyl), —SO($C_1$–$C_4$ alkyl), —$SO_2$($C_1$–$C_4$)alkyl, —CO($C_1$–$C_4$ alkyl), —C(=O)H or —C(=O)O($C_1$–$C_4$alkyl), wherein each of the ($C_1$–$C_6$ alkyl) and ($C_1C_4$ alkyl) moieties in the foregoing $R^4$ groups may optionally contain one or two double or triple bonds and may optionally be substituted with one or two substituents independently selected from hydroxy, amino, $C_1$–$C_3$ alkoxy, dimethylamino, methylamino, ethylamino, —NHC(=O)$CH_3$, fluoro, chloro, $C_1$–$C_3$ thioalkyl, —CN, —COOH, —C(=O)O($C_1$–$C_4$ alkyl), —C(=O)($C_1$–$C_4$ alkyl) and —$NO_2$;

$R^5$ is phenyl, naphthyl, thienyl, benzothienyl, pyridyl, quinolyl, pyrazinyl, furanyl, benzofuranyl, benzothiazolyl, benzisothiazolyl, benzisoxazolyl, benzimidazolyl, indolyl, benzoxazolyl or $C_3$–$C_8$ cycloalkyl wherein one or two of the carbon atoms of said cycloalkyl rings that contain at least 5 ring members may optionally and independently be replaced by an oxygen or sulfur atom or by $NZ^4$ wherein $Z^4$ is hydrogen, $C_1$–$C_4$ alkyl or benzyl; and wherein each of the foregoing $R^5$ groups is substituted with from one to four substituents $R^{12}$ wherein one to three of said substituents may be selected, independently, from chloro, $C_1$–$C_6$ alkyl and —O($C_1$–$C_6$ alkyl) and one of said substituents may be selected from bromo, iodo, formyl, —CN, —$CF_3$, —$NO_2$, —$NH_2$, —NH($C_1$–$C_4$ alkyl), —N($C_1$–$C_2$ alkyl)($C_1$–$C_6$ alkyl), —C(=O)O($C_1$–$C_4$ alkyl), —C(=O)($C_1$–$C_4$ alkyl), —COOH, —$SO_2$NH($C_1$–$C_4$ alkyl), —$SO_2$N($C_1$–$C_2$ alkyl)($C_1$–$C_4$ alkyl), —$SO_2NH_2$—NH$SO_2$($C_1$–$C_4$ alkyl), —S($C_1$–$C_6$ alkyl) and —$SO_2$($C_1$–$C_6$ alkyl), and wherein each of the $C_1$–$C_4$ alkyl and $C_1$–$C_6$ alkyl moieties in the foregoing $R^5$ groups may optionally be substituted with one or two substituents independently selected from fluoro, hydroxy, amino, methylamino, dimethylamino and acetyl;

$R^7$ is hydrogen, $C_1$–$C_4$ alkyl, halo, cyano, hydroxy, —O($C_1$–$C_4$ alkyl) —C(=O)($C_1$–$C_4$ alkyl), —C(=O)O($C_1$–$C_4$alkyl), —$OCF_3$, —$CF_3$, —$CH_2$OH, —$CH_2$O($C_1$–$C_4$ alkyl);

$R^{10}$ is hydrogen, hydroxy, methoxy or fluoro;

$R^{11}$ is hydrogen or $C_1$–$C_4$ alkyl; and

Z is NH, oxygen, sulfur, —N($C_1$–$C_4$ alkyl), —NC(=O)($C_1$–$C_2$ alkyl), NC(=O)O($C_1$–$C_2$alkyl) or $CR^{13}R^{14}$ wherein $R^{13}$ and $R^{14}$ are independently selected from hydrogen, trifluoromethyl and methyl with the exception that one of $R^{13}$ and $R^{14}$ can be cyano;

with the proviso that: (a) in the five membered rings of structures I, II and III, there can not be two double bonds adjacent to each other; and (b) when $R^4$ is attached to nitrogen, it is not halo, cyano or nitro;

or a pharmaceutically acceptable salt of such compound.

VI. The CRF antagonist can also be of the following formula, disclosed in WO 98/05661:

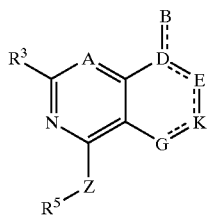

wherein the dashed lines represent optional double bonds;

A is nitrogen or $CR^7$;

B is $-NR^1R^2$, $-CR^1R^2R^{10}$, $-C(=CR^2R^{11})R^1$, $-NHCR^1R^2R^{10}$, $-OCR^1R^2R^{10}$, $-SCR^1R^2R^{10}$, $-CR^2R^{10}NHR^1$, $-CR^2R^{10}OR^1$, $-CR^2R^{10}SR^1$ or $-COR^2$, and is single bonded to D; or B is $-CR^1R^2$, and is double bonded to D and D is carbon;

D is nitrogen or $CR^4$ and is single bonded to all atoms to which it is attached, or D is carbon and is double bonded to E or double bonded to B;

E is oxygen, nitrogen, sulfur, C=O, C=S, $CR^6R^{12}$, $NR^6$ or $CR^6$; or E is a two atom spacer, wherein one of the atoms is oxygen, nitrogen, sulfur, C=O, C=S, $CR^6R^{12}$, $NR^6$ or $CR^6$, and the other is $CR^6R^{12}$ or $CR^9$;

K and G are each, independently, C=O, C=S, sulfur, oxygen, $CHR^8$ or $NR^8$ when single bonded to both adjacent ring atoms, or nitrogen or $CR^8$ when it is double bonded to an adjacent ring atom;

the 6- or 7-membered ring that contains D, E, K and G may contain from one to three double bonds, from zero to two heteroatoms selected from oxygen, nitrogen and sulfur, and from zero to two C=O or C=S groups, wherein the carbon atoms of such groups are part of the ring and the oxygen and sulfur atoms are substituents on the ring;

$R^1$ is $C_1$–$C_6$ alkyl optionally substituted with from one or two substituents independently selected from hydroxy, fluoro, chloro, bromo, iodo, $C_1$–$C_4$ alkoxy, $CF_3$, $-C(=O)(C_1$–$C_4$alkyl), $-C(=O)$-O-$(C_1$–$C_4)$alkyl, $-OC(=O)(C_1$–$C_4$ alkyl), $-OC(=O)N(C_1$–$C_4$ alkyl)$(C_1$–$C_2$ alkyl), $-NHCO(C_1$–$C_4$ alkyl), $-COOH$, $-COO(C_1$–$C_4$ alkyl), $-CONH(C_1$–$C_4$ alkyl), $-CON(C_1$–$C_4$ alkyl)$(C_1$–$C_2$ alkyl), $-S(C_1$–$C_4$ alkyl), $-CN$, $-NO_2$, $-SO(C_1$–$C_4$ alkyl), $-SO_2(C_1$–$C_4$ alkyl), $-SO_2NH(C_1$–$C_4$ alkyl) and $-SO_2N(C_1$–$C_4$ alkyl)$(C_1$–$C_2$ alkyl), wherein each of the $C_1$–$C_4$ alkyl groups in the foregoing $R^1$ groups may optionally contain one or two double or triple bonds;

$R^2$ is $C_1$–$C_{12}$ alkyl which may optionally contain from one to three double or triple bonds, aryl or $(C_1$–$C_4$ alkylene)aryl, wherein said aryl and the aryl moiety of said $(C_1$–$C_4$ alkylene)aryl is selected from phenyl, naphthyl, thienyl, benzothienyl, pyridyl, quinolyl, pyrazinyl, pyrimidinyl, imidazolyl, furanyl, benzofuranyl, benzothiazolyl, isothiazolyl, pyrazolyl, pyrrolyl, indolyl, pyrrolopyridyl, oxazolyl and benzoxazolyl; $C_3$–$C_8$ cycloalkyl or $(C_1$–$C_6$ alkylene)$(C_3$–$C_8$ cycloalkyl), wherein one or two of the carbon atoms of said cycloalkyl and the 5 to 8 membered cycloalkyl moieties of said $(C_1$–$C_6$ alkylene)$(C_3$–$C_8$ cycloalkyl may optionally and independently be replaced by an oxygen or sulfur and wherein each of the foregoing $R^2$ groups may optionally be substituted with from one to three substituents independently selected from chloro, fluoro, hydroxy and $C_1$–$C_4$ alkyl, or with one substituent selected from $C_1$–$C_6$ alkoxy, $-OC(=O)(C_1$–$C_6$ alkyl), $-OC(=O)N(C_1$–$C_4$ alkyl)$(C_1$–$C_2$ alkyl), $-S(C_1$–$C_6$ alkyl), amino, $-NH(C_1$–$C_2$ alkyl), $-N(C_1$–$C_2$ alkyl)$(C_1$–$C_4$ alkyl), $-N(C_1$–$C_4$ alkyl)-CO–$(C_1$–$C_4$ alkyl), $-NHCO(C_1$–$C_4$ alkyl), $-COOH$, $-COO(C_1$–$C_4$ alkyl), $-CONH(C_1$–$C_4$ alkyl), $-CON(C_1$–$C_4$ alkyl)$(C_1$–$C_2$ alkyl), $-SH$, $-CN$, $-NO_2$, $-SO(C_1$–$C_4$ alkyl), $-SO_2(C_1$–$C_4$ alkyl), $-SO_2NH(C_1$–$C_4$ alkyl) and $-SO_2N(C_1$–$C_4$ alkyl)$(C_1$–$C_2$ alkyl);

$-NR^1R^2$ or $CR^1R^2R^{10}$ may form a ring selected from saturated 3 to 8 membered rings, the 5 to 8 membered rings of which may optionally contain one or two double bonds, and wherein one or two of the ring carbon atoms of such 5 to 8 membered rings may optionally and independently be replaced by an oxygen or sulfur atom or by $NZ^3$ wherein $Z^3$ is hydrogen or $C_1$–$C_4$ alkyl;

$R^3$ is hydrogen, $C_1$–$C_4$ alkyl, $-O(C_1$–$C_4$ alkyl), chloro, fluoro, bromo, iodo, $-S(C_1$–$C_4$ alkyl) or $-SO_2(C_1$–$C_4$ alkyl);

$R^4$ is hydrogen, $C_1$–$C_2$ alkyl, hydroxy or fluoro;

each $R^6$, $R^8$ and $R^9$ that is attached to a carbon atom is selected, independently, from hydrogen, $C_1$–$C_2$ alkyl, fluoro, chloro, bromo, iodo, hydroxy, hydroxymethyl, formyl, trifluoromethyl, cyano, amino, nitro, $-O(C_1$–$C_2$ alkyl), $-N(C_1$–$C_2$ alkyl)$(C_1$–$C_2$ alkyl), $-S(C_1$–$C_2$ alkyl), $-CO(C_1$–$C_2$ alkyl), $-C(=O)H$ or $-C(=O)O(C_1$–$C_2$ alkyl), wherein each of the $C_1$–$C_2$ alkyl moieties in the foregoing $R^6$, $R^8$, and $R^9$ groups may optionally contain one double or triple bond; and each $R^6$, $R^8$, and $R^9$ that is attached to a nitrogen atom is selected, independently, from hydrogen and $C_1$–$C_4$ alkyl;

$R^5$ is substituted phenyl, naphthyl, pyridyl or pyrimidyl, wherein each of the foregoing $R^5$ groups is substituted with from two to four substituents $R^{15}$, wherein from one to three of said substituents may be selected, independently, from chloro, $C_1$–C6 alkyl, $-O(C_1$–$C_6$ alkyl) and $-(C_1$–$C_6$alkylene)O$(C_1$–$C_6$alkyl), and wherein one of said substituents may be selected, independently, from bromo, iodo, formyl, cyano, trifluoromethyl, nitro, amino, $-NH(C_1$–$C_4$ alkyl), $-N(C_1$–$C_2$ alkyl)$(C_1$–$C_6$ alkyl), $-C(=O)O(C_1$–$C_4$ alkyl), $-C(=O)(C_1$–$C_4$ alkyl), $-COOH$, $-SO_2NH(C_1$–$C_4$ alkyl), $-SO_2N(C_1$–$C_2$ alkyl)$(C_1$–$C_4$ alkyl), $-SO_2NH_2$, $-NHSO_2(C_1$–$C_4$ alkyl), $-S(C_1$–$C_6$ alkyl) and $-SO_2(C_1$–$C_6$ alkyl), and wherein each of the $C_1$–$C_4$ alkyl and $C_1$–$C_6$ alkyl moieties in the foregoing $R^5$ groups may optionally be substituted with one or two substituents independently selected from fluoro, hydroxy, amino, methylamino, dimethylamino and acetyl;

$R^7$ is hydrogen, methyl, halo (e.g., chloro, fluoro, iodo or bromo), hydroxy, methoxy, $-C(=O)(C_1$–$C_2$ alkyl), $-C(=O)O(C_1$–$C_2$ alkyl), trifluoromethoxy, hydroxymethyl, trifluoromethyl or formyl;

$R^{10}$ is hydrogen, hydroxy, methoxy or fluoro, $R^{11}$ is hydrogen or $C_1$–$C_4$ alkyl;

$R^{12}$ is, hydrogen or methyl; and

Z is NH, oxygen, sulfur, $-N(C_1$–$C_4$ alkyl), or $CR^{13}R^{14}$ wherein $R^{13}$ and $R^{14}$ are independently selected from hydrogen, and methyl with the exception that one of $R^{13}$ and $R^{14}$ may optionally be cyano;

with the proviso that: (a) in the six or seven membered rings of structures in formula I, there can not be two double bonds adjacent to each other; and (b) when D is carbon and is double bonded to B, then B is $CR^1R^2$;

or a pharmaceutically acceptable salt of such compound.

VII. The CRF antagonist can also be of the following formula, disclosed in WO 98/08847:

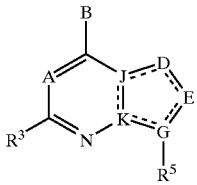

or a pharmaceutically acceptable salt thereof, wherein the dashed lines represent optional double bonds;

A is nitrogen or $CR^7$;

B is $-NR^1R^2$, $-CR^1R^2R^{10}$ $-C(=CR^2R^{11})R^1$, $-NHCR^1R^2R^{10}$, $-OCR^1R^2R^{10}$, $SCR^1R^2R^{10}$, $-CR^2R^{10}NHR^1$, $-CR^2R^{10}OR^1$, $-CR^2R^{10}$, $SR^1$ or $-COR^2$;

J and K are each independently nitrogen or carbon and both J and K are not nitrogens;

D and E are each selected, independently, from nitrogen, $CR^4$, $C=O$, $C=S$, sulfur, oxygen, $CR^4R^6$ and $NR^8$;

G is nitrogen or carbon;

the ring containing D, E, G, K, and J in formula I may be a saturated or unsaturated 5-membered ring and may optionally contain one or two double bonds and may optionally contain from one to three heteroatoms in the ring and may optionally have one or two $C=O$ or $C=S$ groups;

$R^1$ is $C_1-C_6$ alkyl optionally substituted with one or two substituents independently selected from hydroxy, fluoro, chloro, bromo, iodo, $-O-(C_1-C_4$ alkyl), $CF_3$, $-C(=O)O-(C_1-C_4$ alkyl), $-OC(=O)(C_1-C_4$ alkyl), $-OC(=O)N(C_1-C_4$ alkyl)$(C_1-C_2$ alkyl), $-NHCO(C_1-C_4$ alkyl), $-COOH$, $-COO(C_1-C$ alkyl), $-CONH(C_1-C_4$ alkyl), $-CON(C_1-C_4$ alkyl)$(C_1-C_2$ alkyl), $-S(C_1-C_4$ alkyl), $-CN$, $-NO_2$, $-SO(C_1-C_4$ alkyl), $-SO_2(C_1-C_4$ alkyl), $-SO_2NH(C_1-C_4$ alkyl) and $-SO_2N(C_1-C_4$ alkyl)$(C_1-C_2$ alkyl), wherein each of the $C_1-C_4$ alkyl groups in the foregoing $R^1$ groups may optionally contain one or two double or triple bonds;

$R^2$ is $C_1-C_{12}$ alkyl which may optionally contain from one to three double or triple bonds, aryl or $(C_1-C_4$ alkylene)aryl, wherein said aryl and the aryl moiety of said $(C_1-C_4$ alkylene)aryl is selected from phenyl, naphthyl, thienyl, benzothienyl, pyridyl, quinolyl, pyrazinyl, pyrimidinyl, imidazolyl, furanyl, benzofuranyl, benzothiazolyl, isothiazolyl, pyrazolyl, pyrrolyl, indolyl, pyrrolopyridyl, oxazolyl and benzoxazolyl; $C_3-C_8$ cycloalkyl or $(C_1-C_6$ alkylene)$(C_3-C_8$ cycloalkyl), wherein one or two of the carbon atoms of said cycloalkyl and the 5 to 8 membered cycloalkyl moieties of said $(C_1-C_6$ alkylene)$(C_3-C_8$ cycloalkyl) may optionally and independently be replaced by an oxygen or sulfur atom or by $NZ^2$ wherein $Z^2$ is selected from hydrogen, $C_1-C_4$ alkyl, benzyl and $C_1-C_4$ alkanoyl, and wherein each of the foregoing $R^2$ groups may optionally be substituted with from one to three substituents independently selected from chloro, fluoro, hydroxy and $C_1-C_4$ alkyl, or with one substituent selected from bromo, iodo, $C_1-C_6$ alkoxy, $-OC(=O)$ ($C_1-C_6$ alkyl), $-OC(=O)N(C_1-C_4$ alkyl)$(C_1-C_2$ alkyl), $-S(C_1-C_6$ alkyl), amino, $-NH(C_1-C_2$ alkyl), $-N(C_1-C_2$ alkyl)$(C_1-C_4$ alkyl), $-N(C_1-C_4$ alkyl)-$CO-(C_1-C_4$ alkyl), $-NHCO(C_1-C_4$ alkyl), $-COOH$, $-COO(C_1-C_4$ alkyl), $-CONH(C_1-C_4$ alkyl), $-CON(C_1-C_4$ alkyl)$(C_1-C_2$ alkyl), $-SH$, $-CN$, $-NO_2$, $-SO(C_1-C_4$ alkyl), $-SO_2(C_1-C_4$ alkyl), $-SO_2NH(C_1-C_4$ alkyl) and $-SO_2N(C_1-C_2$ alkyl);

$-NR^1R^2$ or $CR^1R^2R^{10}$ may form a saturated 3 to 8 membered carbocyclic ring which may optionally contain from one to three double bonds and wherein one or two of the ring carbon atoms of such 5 to 8 membered rings may optionally and independently be replaced by an oxygen or sulfur atom or by $NZ^3$ wherein $Z^3$ is hydrogen, $C_1-C_4$ alkyl, benzyl or $C_1-C_4$ alkanoyl;

$R^3$ is hydrogen, $C_1-C_4$ alkyl, $-O(C_1-C_4$ alkyl), chloro, fluoro, bromo, iodo, $(C_1-C_2$ alkylene)-O-$(C_1-C_2$ alkyl), $(C_1-C_2$ alkylene)-OH, or $-S(C_1-C_4$ alkyl);

each $R^4$ is, independently, hydrogen, $(C_1-C_6$ alkyl), fluoro, chloro, bromo, iodo, hydroxy, cyano, amino, $(C_1-C_2$ alkylene)-OH, $CF_3$, $CH_2SCH_3$, nitro, $-O(C_1-C_4$ alkyl), $-N(C_1-C_4$ alkyl)$(C_1-C_2$ alkyl), $-S(C_1-C_4$ alkyl), $-CO(C_1-C_4$ alkyl), $-C(=O)H$ or $-C(=O)O(C_1-C_4$ alkyl);

$R^6$ is hydrogen, methyl or ethyl;

$R^8$ is hydrogen or $C_1-C_4$ alkyl;

$R^5$ is phenyl, pyridyl, pyrazinyl, pyrimidyl, pyridazinyl and wherein each of the foregoing $R^5$ groups is substituted with from one to four substituents $R^{13}$ wherein one to three of said substituents may be selected, independently, from fluoro, chloro, $C_1-C_6$ alkyl and $-O(C_1-C_6$ alkyl) and one of said substituents may be selected from bromo, iodo, formyl, OH, $(C_1-C_4$ alkylene)-OH, $(C_1-C_4$ alkylene)-O-$(C_1-C_2$ alkyl), $-CN$, $-CF_3$, $-NO_2$, $-NH_2$, $-NH(C_1-C_4$ alkyl), $-N(C_{1-2}$ alkyl)$(C_1-C_6$ alkyl), $-OCO(C_1-C_4$ alkyl), $(C_1-C_4$ alkylene)-O-$(C_1-C_4$ alkyl), $-S(C_1-C_6$ alkyl), $(C_1-C_4$ alkylene)-S-$(C_1-C_4$ alkyl), $-C(=O)O(C_1-C_4$ alkyl), $-C(=O)(C_1-C_4$ alkyl), $-COOH$, $-SO_2NH(C_1-C_4$ alkyl), $-SO_2N(C_1-C_2$ alkyl)$(C_1-C_4$ alkyl), $-SO_2NH_2$, $-NHSO_2(C_1-C_4$ alkyl), $-S(C_1-C_6$ alkyl) and $-SO_2(C_1-C_6$ alkyl), and wherein each of the $C_1-C_4$ alkyl and $C_1-C_6$ alkyl moieties in the foregoing $R^5$ groups may optionally have one or two double bonds;

$R^7$ is hydrogen, $C_1-C_4$ alkyl, halo (e.g., chloro, fluoro, iodo or bromo), hydroxy, $-O(C_1-C_4$ alkyl), $-C(=O)$ ($C_1-C_4$ alkyl), $-C(=O)O(C_1-C_4$ alkyl), $-OCF_3$, $-CF_3$, $-CH_2OH$ or $-CH_2O(C_1-C_2$ alkyl);

$R^{10}$ is hydrogen, hydroxy, methoxy or fluoro;

$R^{11}$ is hydrogen or $C_1-C_4$ alkyl; and with the proviso that: a) when both J and K are carbons and D is $CR^4$ and E is nitrogen, then G can not be nitrogen; (b) when both J and K are carbons and D and G are nitrogens, then E can not be $CR^4$ or $C=O$ or $C=S$; (c) when both J and K are carbons and D and E are carbons, then G can not be nitrogen; (d) when G is carbon, it must be double banded to E; and (e) in the ring containing J, K, D, E and G, there can not be two double bonds adjacent to each other;

and the pharmaceutically acceptable salts of such compounds.

VIII. Other useful CRF antagonists are of the following formula, disclosed in WO 98/08846:

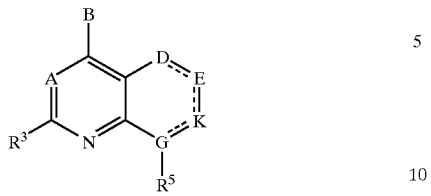

wherein the dashed lines represent optional double bonds;

A is nitrogen or $CR^7$;

B is $-NR^1R^2$, $-CR^1R^2R^{10}$, $-C(=CR^2R^{11})R^1$, $-NHCR^1R^2R^{10}$, $-OCR^1R^2R^{10}$, $-SCR^1R^2R^{10}$, $-CR^2R^{10}NHR^1$, $-CR^2R^{10}OR^1$, $-CR^2R^{10}SR^1$ or $-COR^2$;

G is nitrogen or $CR^4$ and is single bonded to all atoms to which it is attached, or G is carbon and is double bonded to K;

K is nitrogen or $CR^6$ when double bonded to G or E, or K is oxygen, sulfur, $C=O$, $C=S$, $CR^6R^{12}$ or $NR^8$ when single bonded to both adjacent ring atoms, or K is a two atom spacer, wherein one of the two ring atoms of the spacer is oxygen, nitrogen, sulfur, $C=O$, $C=S$, $CR^6R^{12}$, $NR^6$ or $CR^6$, and the other is $CR^6R^{12}$ or $CR^9$;

D and E are each, independently, $C=O$, $C=S$, sulfur, oxygen, $CR^4R^6$ or $NR^8$ when single bonded to both adjacent ring atoms, or nitrogen or $CR^4$ when it is double bonded to an adjacent ring atom;

the 6- or 7-membered ring that contains D, E, K and G may contain from one to three double bonds, from zero to two heteroatoms selected from oxygen, nitrogen and sulfur, and from zero to two $C=O$ or $C=S$ groups, wherein the carbon atoms of such groups are part of the ring and the oxygen and sulfur atoms are substituents on the ring;

$R^1$ is $C_1-C_6$ alkyl optionally substituted with from one or two substituents independently selected from hydroxy, fluoro, chloro, bromo, iodo, $C_1-C_4$ alkoxy, $CF_3$, $-C(=O)(C_1-C_4$ alkyl), $-C(=O)-O-(C_1-C_4)$alkyl, $-OC(=O)(C_1-C_4$ alkyl), $-OC(=O)N(C_1-C_4$ alkyl) $(C_1-C_2$ alkyl), $-NHCO(C_1-C_4$ alkyl), $-COOH$, $-COO(C_1-C_4$ alkyl), $-CONH(C_1-C_4$ alkyl), $-CON(C_1-C_4$ alkyl)$(C_1-C_2$ alkyl), $-S(C_1-C_4$ alkyl), $-CN$, $-NO_2$, $-SO(C_1-C_4$ alkyl), $-SO_2(C_1-C_4$ alkyl), $-SO_2NH(C_1-C_4$ alkyl) and $-SO_2N(C_1-C_4$ alkyl) $(C_1-C_2$ alkyl), wherein each of the $C_1-C_4$ alkyl groups in the foregoing $R^1$ groups may optionally contain one or two double or triple bonds;

$R^2$ is $C_1-C_{12}$ alkyl which may optionally contain from one to three double or triple bonds, aryl or $(C_1-C_4$ alkylene)aryl, wherein said aryl and the aryl moiety of said $(C_1-C_4$ alkylene)aryl is selected from phenyl, naphthyl, thienyl, benzothienyl, pyridyl, quinolyl, pyrazinyl, pyrimidinyl, imidazolyl, furanyl, benzofuranyl, benzothiazolyl, isothiazolyl, pyrazolyl, pyrrolyl, indolyl, pyrrolopyridyl, oxazolyl and benzoxazolyl; $C_3-C_8$ cycloalkyl or $(C_1-C_6$ alkylene)$(C_3-C_8$ cycloalkyl), wherein one or two of the carbon atoms of said cycloalkyl and the 5 to 8 membered cycloalkyl moieties of said $(C_1-C_6$ alkylene)$(C_3-C_8$ cycloalkyl may optionally and independently be replaced by an oxygen or sulfur atom or by NZ wherein Z is hydrogen, $C_1-C_4$ alkyl or benzyl, and wherein each of the foregoing $R^2$ groups may optionally be substituted with from one to three substituents independently selected from chloro, fluoro, hydroxy and $C_1-C_4$ alkyl, or with one substituent selected from $C_1-C_6$ alkoxy, $-OC(=O)(C_1-C_6$ alkyl), $-OC(=O)N(C_1-C_4$ alkyl) $(C_1-C_2$ alkyl), $-S(C_1-C_6$ alkyl), amino, $-NH(C_1-C_2$ alkyl), $-N(C_1-C_2$ alkyl)$(C_1-C_4$ alkyl), $-N(C_1-C_4$ alkyl)$-CO-(C_1-C_4$ alkyl), $-NHCO(C_1-C_4$ alkyl), $-COOH$, $-COO(C_1-C_4$ alkyl), $-CONH(C_1-C_4$ alkyl), $-CON(C_1-C_4$ alkyl)$(C_1-C_2$ alkyl), $-SH$, $-CN$, $-NO_2$, $-SO(C_1-C_4$ alkyl), $-SO_2(C_1-C_4$ alkyl), $-SO_2NH(C_1-C_4$ alkyl) and $-SO_2N(C_1-C_4$ alkyl)$(C_1-C_2$ alkyl);

$-NR^1R^2$ or $CR^1R^2R^{10}$ may form a ring selected from saturated 3 to 8 membered rings, the 5 to 8 membered rings of which may optionally contain one or two double bonds, and wherein one or two of the ring carbon atoms of such 5 to 8 membered rings may optionally and independently be replaced by an oxygen or sulfur atom or by $NZ^2$ wherein $Z^2$ is hydrogen, benzyl or $C_1-C_4$ alkyl;

$R^3$ is hydrogen, $C_1-C_4$ alkyl, $-O(C_1-C_4$ alkyl), chloro, fluoro, bromo, iodo, $-S(C_1-C_4$ alkyl) or $-SO_2(C_1-C_4$ alkyl);

each $R^8$, $R^9$ and $R^{12}$ is selected, independently, from hydrogen and $C_1-C_2$ alkyl;

each $R^4$ and $R^6$ that is attached to a carbon atom is selected, independently, from hydrogen and $C_1-C_6$ alkyl, fluoro, chloro, bromo, iodo, hydroxy, hydroxy $(C_1-C_2$ alkyl), trifluoromethyl, cyano, amino, nitro, $-O(C_1-C_4$ alkyl), $-N(C_1-C_4$ alkyl)$(C_1-C_2$ alkyl), $-CH_2SCH_3$, $-S(C_1-C_4$ alkyl), $-CO(C_1-C_4$ alkyl), $-C(=O)H$ or $-C(=O)O(C_1-C_4$ alkyl), wherein each of the $C_1-C_2$ alkyl moieties in the foregoing $R^4$ and $R^6$ groups may optionally contain one double or triple bond; and $R^6$, when attached to a nitrogen atom, is selected from hydrogen and $C_1-C_4$ alkyl;

$R^5$ is substituted phenyl, naphthyl, pyridyl or pyrimidyl, wherein each of the foregoing $R^5$ groups is substituted with from two to four substituents $R^{13}$, wherein up to three of said substituents may be selected, independently, from chloro, $C_1-C_6$ alkyl, $-O(C_1-C_6$ alkyl) and $-C_1-C_6$ alkylene)O(C_1-C_6$alkyl), and wherein one of said substituents may be selected, independently, from bromo, iodo, formyl, cyano, trifluoromethyl, nitro, amino, $-NH(C_1-C_4$ alkyl), $-N(C_1-C_2$ alkyl)$(C_1-C_6$ alkyl), $-C(=O)O(C_1-C_4$ alkyl), $-C(=O)(C_1-C_4$ alkyl), $-COOH$, $-SO_2NH$ $(C_1-C_4$ alkyl), $-SO_2N(C_1-C_2$ alkyl)$(C_1-C_4$ alkyl), $-SO_2NH_2$, $-NHSO_2(C_1-C_4$ alkyl), $-C_0-C_1$ alkylene)$-S-(C_1-C_2$ alkyl), $-(C_0-C_1$ alkylene)$-SO-(C_1-C_2$ alkyl), $-(C_0-C_1$ alkylene)$-SO_2-(C_1-C_2$ alkyl) and $-(C_1-C_4$ alkylene)$-OH$, and wherein each of the $C_1-C_4$ alkyl and $C_1-C_6$ alkyl moieties in the foregoing $R^5$ groups may optionally be substituted with one or two substituents independently selected from fluoro, hydroxy, amino, methylamino, dimethylamino and acetyl;

$R^7$ is hydrogen, methyl, halo (e.g., chloro, fluoro, iodo or bromo), hydroxy, methoxy, $-C(=O)(C_1-C_2$ alkyl), $-C(=O)O(C_1-C_2$ alkyl), hydroxymethyl, trifluoromethyl or formyl;

$R^{10}$ is hydrogen, hydroxy, methoxy or fluoro; and $R^{11}$ is hydrogen or $C_1$–$C_4$ alkyl;

with the proviso that in the ring containing D, E, K and G of formula I, there can not be two double bonds adjacent to each other;

and the pharmaceutically acceptable salt of such compound.

IX. The CRF antagonist may also be of the following formula, disclosed in WO 95/10506:

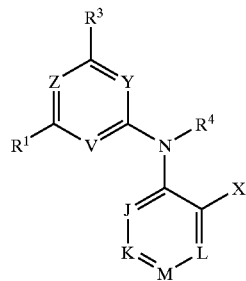

or a pharmaceutically, acceptable salt or prodrug thereof, wherein Y is $CR^{3a}$, N, or $CR^{29}$;

when Y is $CR^{3a}$ or N:

$R^1$ is independently selected at each occurrence from the group consisting of $C_1$–$C_4$ alkyl, $C_2$–$C_4$ alkenyl, $C_2$–$C_4$ alkynyl, halogen, $C_1$–$C_2$ haloalkyl, $NR^6R^7$, $OR^8$, and $S(O)_n$ $R^8$; $R^3$ is $C_1$–$C_4$ alkyl, aryl, $C_3$–$C_6$ cycloalkyl, $C_1$–$C_2$ haloalkyl, halogen, nitro, $NR^6R^7$, $OR^8$, $S(O)_nR^8$ $C(=O)R^9$, $C(=O)NR^6R^7$, $C(=S)NR^6R^7$, —(CHR$^{16}$)$_k$NR$^6$R$^7$, (CH$_2$)$_k$ OR$^8$, $C(=O)NR^{10}CH(R^{11})CO_2R^{12}$, —C(OH)(R$^{25}$)(R$^{25a}$), —(CH$_2$)$_p$S(O)$_n$-alkyl, (CHR$^{16}$)R$^{25}$, —C(CN)(R$^{25}$)(R$^{16}$) provided that R$^{25}$ is not —NH— containing rings, —C(=O)R$^{25}$, —CH(CO$_2$R$^{16}$)$_2$, NR$^{10}$ C(=O)CH(R$^{11}$) NR$^{10}$R$^{12}$, NR$^{10}$CH(R$^{11}$)CO$_2$R$^{12}$; substituted $C_1$–$C_4$ alkyl, substituted $C_2$–$C_4$ alkenyl, substituted $C_2$–$C_4$ alkynyl, substituted $C_1$–$C_4$ alkoxy, aryl-(substituted $C_1$–$C_4$) alkyl, aryl-(substituted $C_1$–$C_4$) alkoxy, substituted $C_3$–$C_6$ cycloalkyl, amino-(substituted $C_1$–$C_4$)alkyl, substituted $C_1$–$C_4$ alkylamino, where substitution by $R^{27}$ can occur on any carbon containing substituent; 2-pyridinyl, imidazolyl, 3-pyridinyl, 4-pyridinyl, 2-methyl-3-pyridinyl, 4-methyl-3-pyridinyl, furanyl, 5-methyl-2-furanyl, 2,5-dimethyl-3-furanyl, 2-thienyl, 3-thienyl 5-methyl-2-thienyl, 2-phenothiazinyl, 4-pyrazinyl, azetidinyl, phenyl, 1H-indazolyl, 2-pyrrolidonyl, 2H,6H-1,5,2-dithiazinyl, 2H-pyrrolyl, 3H-indolyl, 4-piperidonyl, 4aH-carbazolyl 4H-quinolizinyl, 6H-1,2,5-thiadiazinyl, acridinyl, azocinyl, azepinyl, benzofuranyl, benzothiophenyl, carbazolyl, chromanyl, chromenyl, cinnolinyl, decahydroquinolinyl, furazanyl, imidazolidinyl, indolinyl, indolizinyl, indolyl, isobenzofuranyl, isochromanyl, isoindolinyl, isoindolyl, isoquinolinyl, benzimidazolyl, isothiazolyl, isoxazolyl, morpholinyl, naphthyridinyl, octahydroisoquinolinyl, oxazolidinyl, oxazolyl, phenanthridinyl, phenanthrolinyl, phenazinyl, phenoxathiinyl, phenoxazinyl, phthalazinyl, piperazinyl, piperidinyl, pteridinyl, purinyl, pyranyl, pyrazolidinyl, pyrazolinyl, pyrazolyl, pyridazinyl, pyrimidinyl, pyrrolidinyl, pyrrolinyl, pyrrolyl, quinazolinyl, quinolinyl, quinoxalinyl, quinuclidinyl, β-carbolinyl, tetrahydrofuranyl, tetrahydroisoquinolinyl, tetrahydroquinolinyl, tetrazolyl, thianthrenyl, thiazolyl, thiophenyl, triazinyl, xanthenyl; or 1-tetrahydroquinolinyl or 2-tetrahydroisoquinolinyl either of which can be substituted with 0–3 groups chosen from keto and $C_1$–$C_4$ alkyl; J, K, and L are independently selected at each occurrence from the group of N, CH, and CX';

M is $CR^5$ or N;

V is $CR^{1a}$ or N;

Z is $CR^2$ or N;

$R^{1a}$, $R^2$, and $R^{3a}$ are independently selected at each occurrence from the group consisting of hydrogen, halo, halomethyl, $C_1$–$C_3$ alkyl, and cyano;

$R^4$ is $(CH_2)_mOR^{16}$, $C_1$–$C_4$ alkyl, allyl, propargyl, $(CH_2)_m$ $R^{13}$, or —$(CH_2)_mOC(O)R^{16}$;

X is halogen, aryl, heteroaryl, $S(O)_2R^8$, $SR^8$, halomethyl, —$(CH_2)_pOR^8$, cyano, —$(CHR^{16})_pNR^{14}R^{15}$, —$C(=O)$ $R^8$, $C_1$–$C_6$ alkyl, $C_4$–$C_{10}$ cycloalkylalkyl, $C_1$–$C_{10}$alkenyl, $C_2$–$C_{10}$alkynyl, $C_2$–$C_{10}$alkoxy, aryl-$(C_2$–$C_{10})$-alkyl, $C_3$–$C_6$cycloalkyl, aryl-$(C_1$–$C_{10})$-alkoxy, nitro, thio-$(C_1$—$C_{10})$-alkyl, —$C(=NOR^{16})$— $C_1$–$C_4$-alkyl, —$C(=NOR^{16})H$, or —$C(=O)NR^{14}R^{15}$, where substitution by $R^{18}$ can occur on any carbon containing substituents;

X' is independently selected at each occurrence from the group consisting of hydrogen, halogen, aryl, heteroaryl, $S(O)_nR^8$, halomethyl, —$(CHR^{16})_pOR^8$, cyano, —$(CHR^{16})_pNR^{14}R^{15}$, $C(=O)R^8$, $C_1$–$C_6$ alkyl, $C_2$–$C_{10}$alkenyl, $C_2$–$C_{10}$alkynyl, $C_1$–$C_{10}$alkoxy, aryl-$(C_1$–$C_{10})$-alkyl, $C_3$–$C_6$cycloalkyl, aryl-$(C_1$–$C_{10})$-alkoxy, nitro, thio-$(C_1$–$C_{10})$-alkyl, —$C(=NOR^{16})$ $C_1$–$C_4$-alkyl, —$C(=NOR^{16})H$, and —$C(=O)$ $NR^{14}R^{15}$, where substitution by $R^{16}$ can occur on any carbon containing substituents;

$R^5$ is halo, —$C(=NOR^{16})$-$C_1$–$C_4$-alkyl, $C_1$–$C_4$alkyl, $C_1$–$C_3$ haloalkyl, —$(CHR^{16})_pOR^8$, —$(CHR^{16})_pS(O)_n$ $R^8$, —$(CHR^6)_pNR^{14}R^{15}$, $C_3$–$C_6$ cycloalkyl, $C_2$–$C_{10}$alkenyl, $C_2$–$C_{10}$alkynyl, $C_2$–$C_{10}$alkynyl, aryl-$(C_2$–$C_{10})$-akyl, aryl-$(C_1$–$C_{10})$-alkoxy, cyano, $C_3$–$C_6$ cycloalkoxy, nitro, amino-$(C_2$–$C_{10})$-alkyl, thio-$(C_2$–$C_{10})$-alkyl, $SO_n(R^8)$, $C(=O)R^8$—$C(=NOR^{16})H$, or —$C(=O)NR^{14}R^{15}$, where substitution by $R^{18}$ can occur on any carbon containing substituents;

$R^6$ and $R^7$ are independently selected at each occurrence from the group consisting of hydrogen, $C_1$–$C_5$ alkyl, $C_3$–$C_{10}$ cycloalkyl, $C_1$–$C_6$ alkoxy, $(C_4$–$C_{12})$-cycloalkylalkyl, —$(CH_2)_kR^{13}$, $(CHR^{16})_pOR^8$, —$(C_1$–$C_6$alkyl)-aryl, heteroaryl, —$S(O)_z$-aryl or —$(C_1$–$C_6$alkyl)-heteroaryl or aryl, wherein the aryl or heteroaryl groups are optionally substituted with 1–3 groups selected from the group consisting of hydrogen, halogen, $C_1$–$C_6$ alkyl, $C_1$–$C_6$ alkoxy, amino, NHC$(=O)(C_1$–$C_6$ alkyl), NH$(C_1$–$C_6$ alkyl), N$(C_1$–$C_6$ alkyl)$_2$, nitro, carboxy, $CO_2(C_1$–$C_6$ alkyl), cyano, and $S(O)_2$ —$(C_1$–$C_6$-alkyl); or can be taken together to form —$(CH_2)_pA(CH_2)_r$—, optionally substituted with 0–3 $R^{17}$; or, when considered with the commonly attached nitrogen, can be taken together to form a heterocycle, said heterocycle being substituted on carbon with 1–3 groups consisting of hydrogen, $C_1$–$C_6$ alkyl, hydroxy, or $C_1$–$C_6$ alkoxy;

A is $CH_2$, O, $NR^{25}$, $C(=O)$, $S(O)_n$, $N(C(=O)R^{17})$, $N(R^{19})$, $C(H)(NR^{14}R^{15})$, $C(H)(OR^{20})$, $C(H)(C(=O)$ $R^{21})$, or $N(S(O)_nR^{21})$;

$R^8$ is independently selected at each occurrence from the group consisting of hydrogen; $C_1$–$C_6$ alkyl; —$(C_4$–$C_{12})$ cycloalkylalkyl; $(CH_2)_kR^{22}$; $C_3$–$C_{10}$ cycloalkyl; —$NR^6R^7$; aryl; heteroaryl; —$NR^{16}(CH_2)_n$ $R^6R^7$; —$(CH_2)_kR^{25}$; and $(CH_2)_k$heteroaryl or $(CH_2)_t$ aryl, either of which can optionally be substituted with 1–3 groups selected from the group consisting of hydrogen, halogen, $C_1$–$C_6$ alkyl, $C_1$–$C_6$ alkoxy, amino, NHC(=O)($C_1$–$C_6$ alkyl), NH($C_1$–$C_6$ alkyl), N($C_1$–$C_6$ alkyl)$_2$, nitro, carboxy, CO$_2$($C_1$–$C_6$ alkyl), cyano, and S(O)$_2$($C_1$–$C_6$-alkyl);

$R^9$ is independently selected at each occurrence from $R^{10}$, hydroxy, $C_1$–$C_4$ alkoxy, $C_3$–$C_6$ cycloalkyl, $C_2$–$C_4$ alkenyl, aryl substituted with 0–3 $R^{18}$, and —($C_1$–$C_6$ alkyl)-aryl substituted with 0–3 $R^{18}$;

$R^{10}$, $R^{16}$, $R^{24}$, and $R^2$ are independently selected at each occurrence from hydrogen or $C_1$–$C_4$ alkyl;

$R^{11}$ is $C_1$–$C_4$ alkyl substituted with 0–3 groups chosen from the following: keto, amino, sulfhydryl, hydroxyl, guanidinyl, p-hydroxyphenyl, imidazolyl, phenyl, indolyl, and indolinyl, or, when taken together with an adjacent $R^{10}$, are (CH$_2$)$_t$;

$R^{12}$ is hydrogen or an appropriate amine protecting group for nitrogen or an appropriate carboxylic acid protecting group for carboxyl;

$R^{13}$ is independently selected at each occurrence from the group consisting of CN, OR$^{19}$, SR$^{19}$, and $C_3$–$C_6$ cycloalkyl;

$R^{14}$ and $R^{15}$ are independently selected at each occurrence from the group consisting of hydrogen, $C_4$–$C_{10}$, cycloalkyl-alkyl, and R$_{19}$;

$R^{17}$ is independently selected at each occurrence from the group consisting of $R^{10}$, $C_1$–$C_4$ alkoxy, halo, OR$^{23}$, SR$^{23}$, NR$^{23}$R$^{24}$, and ($C_1$–$C_6$) alkyl ($C_1$–$C_4$) alkoxy;

R$_{18}$ is independently selected at each occurrence from the group consisting of $R^{10}$, hydroxy, halogen, $C_1$–$C_2$ haloalkyl, $C_1$–$C_4$ alkoxy, C(=O)R$^{24}$, and cyano;

$R^{19}$ is independently selected at each occurrence from the group consisting of $C_1$–$C_6$ alkyl, $C_3$–$C_6$ cycloalkyl, (CH$_2$)$_w$R$^{22}$, and aryl substituted with 0–3 $R^{18}$;

$R^{20}$ is independently selected at each occurrence from the group consisting of $R^{10}$, C(=O)R$^{31}$, and $C_2$–$C_4$ alkenyl;

$R^{21}$ is independently selected at each occurrence from the group consisting of $R^{10}$, $C_1$–$C_4$ alkoxy, NR$^{23}$R$^{24}$, and hydroxyl;

$R^{22}$ is independently selected at each occurrence from the group consisting of cyano, OR$^{24}$, SR$^{24}$, NR$^{23}$R$^{24}$, $C_1$–$C_6$ alkyl, $C_3$–$C_6$ cycloalkyl, —S(O)$_n$R$^{31}$, and —C(=O)R$^{25}$;

$R^{25}$, which can be optionally substituted with 0–3 $R^{17}$, is independently selected at each occurrence from the group consisting of phenyl, pyrazolyl, imidazolyl, 2-methyl-3-pyridinyl, 4-methyl-3-pyridinyl, furanyl, 5-methyl-2-furanyl, 2,5-dimethyl-3-furanyl 2-thienyl, 3-thienyl, 5-methyl-2-thienyl, 2-pheno-thiazinyl, 4-pyrazinyl, azetidinyl, 1H-indazolyl, 2-pyrrolidonyl, 2H,6H-1,5,2-dithiazinyl, 2H-pyrrolyl, 3H-indolyl, 4-piperidonyl, 4aH-carbazolyl, 4H-quinolizinyl, 6H-1,2,5-thiadiazinyl, acridinyl, azocinyl, azepinyl, benzofuranyl, benzothiophenyl, carbazolyl, chromanyl, chromenyl, cinnolinyl, decahydroquinolinyl, furazanyl, indolinyl, indolizinyl, indolyl, isobenzofuranyl, isochromanyl, isoindolinyl, isoindolyl, isoquinolinyl benzimidazolyl, isothiazolyl, isoxazolyi, morpholinyl, naphthyridinyl, octahydroisoquinolinyl, oxazolidinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazolidinyl, pyridazinyl, pyridyl, pyrimidinyl, pyrrolidinyl, pyrrolinyl, pyrrolyl, quinazolinyl, quinolinyl, quinoxalinyl, quinuclidinyl, B-carbolinyl, tetrahydrofuranyl, tetrazolyl, thianthrenyl, thiazolyl, thiophenyl, triazinyl, xanthenyl; and 1-tetrahydroquinolinyl or 2-tetrahydroisoquinolinyl either of which can be substituted with 0–3 groups chosen from keto and $C_1$–$C_4$ alkyl;

$R^{25a}$, which can be optionally substituted with 0–3 $R^{17}$, is independently selected at each occurrence from the group consisting of H and $R^{25}$;

$R^{27}$ is independently selected at each occurrence from the group consisting of $C_1$–$C_3$ alkyl, $C_2$–$C_4$ alkenyl, $C_2$–$C_4$ alkynyl, $C_2$–$C_4$ alkoxy, aryl, nitro, cyano, halogen, aryloxy, and heterocycle optionally linked through 0;

$R^{31}$ is independently selected at each occurrence from the group consisting of $C_1$–$C_4$ alkyl, $C_3$–$C_7$ cycloalkyl, $C_4$–$C_{10}$ cycloalkyl-alkyl, and aryl-($C_1$–$C_4$) alkyl;

k, m, and r are independently selected at each occurrence from 1–4;

n is independently, selected at each occurrence from 0–2, p, q, and z are independently selected at each occurrence from 0–3;

t and w are independently selected at each occurrence from 1–6, provided that when J is CX' and K and L are both CH, and M is CR$^5$, then (A) when V and Y are N and Z is CH and $R^1$ and $R^3$ are methyl,
  (1) and $R^4$ is methyl, then
    (a) $R^5$ can not be methyl when X is OH and X' is H;
    (b) R can not be —NHCH$_3$, or —N(CH$_3$)$_2$ when X and X' are —OCH$_3$; and
    (c) $R^5$ can not be —N(CH$_3$)$_2$ when X and X' are —OCH$_2$CH$_3$;
  (2) and $R^4$ is ethyl, then
    (a) $R^5$ can not be methylamine when X and X' are —OCH$_3$;
    (b) $R^5$ can not be OH when X is Br and X' is OH; and
    (c) $R^5$ can not be —CH$_2$OH or —CH$_2$N(CH$_3$)$_2$ when X is —SCH$_3$ and X' is H;

(B) when V and Y are N, Z is CH, $R^4$ is ethyl, $R^5$ is iso-propyl, X is Br, X' is H, and
  (1) $R^1$ is CH$_3$, then
    (a) $R^3$ can not be OH, piperazin-1-yl, —CH$_2$-piperidin-1-yl, —CH$_2$—(N-4-methylpiperazin-1-yl), —C(O)NH-phenyl, —CO$_2$H, —CH$_2$O-(4-pyridyl), —C(O)NH$_2$, 2-indolyl, —CH$_2$O-(4-carboxyphenyl), —N(CH$_2$CH$_3$)(2-bromo4-isopropylphenyl);
  (2) $R^2$ is —CH$_2$CH$_2$CH$_3$ then $R^3$ can not be —CH$_2$CH$_2$CH$_3$ (C) when V, Y and Z are N, $R^4$ is ethyl, and
  (1) $R^5$ is iso-propyl, X is bromo, and X' is H, then
    (a) $R^3$ can not be OH or —OCH$_2$CN when $R^1$ is CH$_3$ and
    (b) $R^3$ can not be —N(CH$_3$)$_2$ when $R^1$ is —N(CH$_3$)$_2$;
  (2) $R^5$ is OCH$_3$, X is —OCH$_3$, and X' is H, then $R^3$ and $R^1$ can not both be chloro; further provided that when J, K, and L are all CH and M is CR$^5$, then (D) at least one of V, Y, and Z must be N;
(E) when V is CR$^{1a}$, Z and Y can not both be N;
(F) when Y is CR, Z and V can not both be N;
(G) when Z is CR$^2$, V and Y must both be N;
(H) Z can be N only when both V and Y are N or when V is CR$^{1a}$ and Y is CR$^{3a}$;

(I) when V and Y are N, Z is $CR^2$, and $R^2$ is H or $C_1$–$C_3$ alkyl, and $R^4$ is $C_1$–$C_3$ alkyl, $R^3$ can not be 2-pyridinyl, indolyl, indolinyl, imidazolyl, 3-pyridinyl, 4-pyridinyl, 2-methyl-3-pyridinyl, 4-methyl-3-pyridinyl, furanyl, 5-methyl-2-furanyl, 2,5-dimethyl-3-furanyl, 2-thienyl, 3-thienyl, 5-methyl-2-thienyl, 2-phenothiazinyl, or 4-pyrazinyl;

(J) when V and Y are N; Z is $CR^2$; $R^2$ is H or $C_1$–$C_3$ alkyl; $R^4$ is $C_1$–$C_4$ alkyl, $R^5$, X, and/or X' are OH, halo, $CF_3$, $C_1$–$C_4$ alkyl, $C_1$–$C_4$ alkoxy, $C_1$–$C_4$ alkylthio, cyano, amino, carbamoyl, or $C_1$–$C_4$ alkanoyl; and $R^1$ is $C_1$–$C_4$ alkyl, then $R^4$ can not be —NH(substituted phenyl) or —N($C_1$–$C_4$ alkyl)(substituted phenyl);

and wherein, when Y is $CR^{29}$:

J, K, L, M, Z, A, k, m, n, p, q, r, t, w, $R^3$, $R^{10}$, $R^{11}$, $R^{12}$, $R^{13}$, $R^{16}$, $R^{18}$, $R^{19}$, $R^{21}$ $R^{23}$, $R^{24}$, $R^{25}$, and $R^{27}$ are as defined above and $R^{25a}$, in addition to being as defined above, can also be $C_1$–$C_4$ alkyl, but V is N;

$R^1$ is $C_1$–$C_2$ alkyl, $C_2$–$C_4$ alkenyl, $C_2$–$C_4$ alkynyl, $C_2$–$C_4$ alkoxy, halogen, amino, methylamino, dimethylamino, aminomethyl, or N-methylaminomethyl;

$R^2$ is independently selected at each occurrence from the group consisting of hydrogen, halo, $C_1$–$C_3$, alkyl, nitro, amino, and —$CO_2R^{10}$;

$R^4$ is taken together with $R^{29}$ to form a 5-membered ring and is —$C(R^{26})$= or —N= when $R^{29}$ is —$C(R^{30})$= or —N=, or —$CH(R^{26})$— when $R^{29}$ is —$CH(R^{30})$—;

X is Cl, Br, I, S(O)n$R^8$, $OR^8$, halomethyl, —$(CHR^{16})_p$ $OR^8$, cyano, —$(CHR^{16})_pNR^{14}R^{15}$, C(=O)$R^8$, $C_1$–$C_6$ alkyl, $C_2$–$C_{10}$ alkenyl, $C_2$–$C_{10}$ alkynyl, $C_1$–$C_{10}$, alkoxy, aryl-($C_1$–$C_{10}$)-alkyl, $C_3$–$C_6$ cycloalkyl, aryl-($C_1$–$C_{10}$)-alkoxy, nitro, thio-($C_1$–$C_{10}$)-alkyl, —C(=NOR$^{16}$)$C_1$–$C_4$-alkyl, —C(=NOR$^{16}$)H, or C(=O)NR$^{14}R^{15}$ where substitution by $R^{18}$ can occur on any carbon containing substituents;

X' is hydrogen, Cl, Br, I, S(O),$R^8$, —$(CHR^{16})_pOR^8$, halomethyl, cyano, —$(CHR^{16})_pNR^{14}R^{15}$, C(=O)$R^8$, $C_1$–$C_{10}$alkyl, $C_2$–$C_{10}$alkenyl, $C_2$–$C_{10}$, alkynyl, $C_1$–$C_{10}$ alkoxy, aryl-($C_1$–$C_{10}$)-alkyl, $C_3$–$C_6$ cycloalkyl, aryl-($C_1C_{10}$)-alkoxy, nitro, thio-($C_2$–$C_{10}$)-alkyl, —C(=NOR$^{16}$)—$C_1$–$C_4$-alkyl, —C(=NOR$^{16}$)H, or C(=O)NR$^8R^{15}$ where substitution by $R^{18}$ can occur on any carbon containing substituents;

$R^5$ is halo, —C(=NOR$^{16}$)—$C_1$–$C_4$-alkyl, $C_1$–$C_6$ alkyl, $C_1$–$C_3$ haloalkyl, $C_1$–$C_6$ alkoxy, (CHR$^{16}$)$_p$OR$^5$, (CHR$^{16}$)$_p$S(O)$_n$R$^8$, (CHR$^{16}$)$_p$NR$^{14}$R$^{15}$, $C_3$–$C_6$ cycloalkyl, $C_2$–$C_{10}$ alkenyl, $C_2$–$C_{10}$ alkynyl, aryl-($C_2$–$C_{10}$)-alkyl, aryl-($C_1$–$C_{10}$)-alkoxy, cyano, $C_3$–$C_6$ cycloalkoxy, nitro, amino-($C_1$–$C_{10}$)-alkyl, thio-($C_1$–$C_{10}$)-alkyl, SO$_n$(R$^8$), C(=O)R$^8$, —C(=NOR$^{16}$)H, or C(=O)NR$^8R^{15}$ where substitution by $R^{18}$ can occur on any carbon containing substituents;

$R^8$ and $R^7$ are independently selected at each occurrence from the group consisting of hydrogen, $C_1$–$C_6$ alkyl, $C_3$–$C^{10}$ cycloalkyl, —$(CH_2)_kR^{13}$, ($C_4$–$C_{12}$)-cycloalkylalkyl, $C_1$–$C^6$ alkoxy, —($C_1$–$C_6$ alkyl)-aryl, heteroaryl, aryl, —S(O)$_z$-aryl or —($C_1$–$C_6$ alkyl)-heteroaryl or aryl wherein the aryl or heteroaryl groups are optionally substituted with 1–3 groups selected from hydrogen, halogen, $C_1$–$C_6$ alkyl, $C_1$–$C_6$ alkoxy, amino, NHC(=O)($C_1$–$C_6$ alkyl), NH($C_1$–$C_6$ alkyl), N($C_1$–$C_6$ alkyl), N($C_1$–$C_6$ alkyl)$_2$, nitro, carboxy, $CO_2$ ($C_1$–$C_6$ alkyl), and cyano; or can be taken together to form —$(CH_2)_qA(CH_2)_r$—, optionally substituted with 0–3 $R^{17}$;

or, when considered with the commonly attached nitrogen, can be taken together to form a heterocycle, said heterocycle being substituted on carbon with 1–3 groups consisting of hydrogen, $C_1$–$C_6$ alkyl, hydroxy, or $C_1$–$C_6$ alkoxy;

$R^8$ is independently selected at each occurrence from the group consisting of hydrogen, $C_1$–$C_6$ alkyl, —($C_4$–$C_{12}$) cycloalkylalkyl, $(CH_2)_rR^{22}$, $C_3$–$C_{10}$ cycloalkyl, —($C_1$–$C_6$ alkyl)-aryl, heteroaryl, —NR$^{16}$, —N(CH$_2$)$_n$ NR$^6R^7$; —$(CH_2)_kR^{25}$, —($C_1$–$C_6$ alkyl)-heteroaryl or aryl optionally substituted with 1–3 groups selected from hydrogen, halogen, $C_1$–$C_6$ alkyl, $C_1$–$C_6$ alkoxy, amino, NHC(=O)($C_1$–$C_6$ alkyl), NH($C_1$–$C_6$ alkyl), N($C_1$–$C_6$alkyl)$_2$, nitro, carboxy, $CO_2$($C_1$–$C_6$ alkyl), and cyano;

$R^9$ is independently selected at each occurrence from $R^{10}$, hydroxy, $C_1$–$C_4$ alkoxy, $C_3$–$C_6$ cycloalkyl, $C_2$–$C_4$ alkenyl, and aryl substituted with 0–3 $R^{18}$;

$R^{14}$ and $R^{15}$ are independently selected at each occurrence from the group consisting of hydrogen, $C_1$–$C_6$ alkyl, $C_3$–$C_6$ cycloalkyl, $(CH_2)_rR^{22}$, and aryl substituted with 0–3 $R_{18}$;

$R^{17}$ is independently selected at each occurrence from the group consisting of $R^{10}$, $C_1$–$C_4$ alkoxy, halo, $OR^{23}$, $SR^{23}$, and $NR^{23}R^{24}$;

$R^{20}$ is independently selected at each occurrence from the group consisting of $R^{10}$, and C(=O)$R^{31}$;

$R^{22}$ is independently selected at each occurrence from the group consisting of cyano, $OR^{24}$, $SR^{24}$, $NR^{23}R^{24}$, $C_3$–$C_6$ cycloalkyl, —S(O)$_nR^{31}$, and —C(=O)$R^{25}$;

$R^{26}$ is hydrogen or halogen;

$R^{28}$ is $C_1$–$C_2$, alkyl, $C_2$–$C_4$ alkenyl, $C_2$–$C_4$ alkynyl, hydrogen, $C_1$–$C_2$ alkoxy, halogen, or $C_2$–$C_4$ alkylamino;

$R^{29}$ is taken together with $R^4$ to form a five membered ring and is: —CH(R$^{30}$)— when $R^4$ is —CH(R$^{28}$)—, —C(R$^{30}$)= or —N= when $R^4$ is —C(R$^{28}$)= or —N=;

$R^{30}$ is hydrogen, cyano, $C_1$–$C_2$ alkyl, $C_1$–$C_2$ alkoxy, halogen, $C_1$–$C_2$ alkenyl, nitro, amido, carboxy, or amino;

$R^{31}$ is $C_1$–$C_4$ alkyl, $C_3$–$C_7$ cycloalkyl, or aryl-(Cl-$C_4$) alkyl; provided that when J, K, and are all CH, M is $CR^5$, Z is CH, $R^3$ is $CH_3$, $R^{28}$ is H, $R^5$ is isopropyl, X is Br, X' is H, and $R^1$ is $CH_3$, then $R^{30}$ can not be H, —$CO_2$H, or —$CH_2NH_2$; and further provided that when J, K and L are all CH; M is $CR^5$; Z is N; and (A) $R^{29}$ is —C(R$^{30}$)=; then one of $R^{28}$ or $R^{30}$ is hydrogen;

(B) $R^{29}$ is N; then $R^3$ is not halo, $NH_2$, $NO_2$, $CF_3$, $CO_2$H, $CO_2$-alkyl, alkyl, acyl, alkoxy, OH, or —(CH$_2$)$_m$Oalkyl;

(C) $R^{29}$ is N; then $R^{28}$ is not methyl if X or X' are bromo or methyl and $R^5$ is nitro; or (D) $R^{29}$ is N; and $R^1$ is $CH_3$; and $R^3$ is amino; then $R^5$ is not halogen or methyl.

Preferred compounds of this group include those wherein:

i) V is N, $R^1$ is methyl; and $R^3$ is aryl, $NR^6R^7$, or $OR^8$;

ii) V is N, $R^1$ is methyl; $R^3$ is aryl, $NR^6R^7$, or $OR^8$; and $R^4$ is methyl or ethyl;

iii) V is N, $R^1$ is methyl; $R^3$ is aryl, $NR^6R^7$, or $OR^8$; $R^4$ is methyl or ethyl; and X is O($C_1$–$C_4$ alkyl), Br, or $C_1$–$C_4$ alkyl;

iv) V is N, $R^1$ is methyl; $R^3$ is aryl, $NR^6R^7$, or $OR^8$; $R^4$ is methyl, ethyl; X is OMe, Br, or ($C_1$–$C_4$ alkyl), M is $C_1$–$C_4$ alkyl, Br, Cl, or O($C_1$–$C_4$ alkyl); and v) V is N, $R_1$ is methyl; $R^3$ is aryl, $NR^6R^7$, $OR^8$; or $R^4$ is methyl, ethyl; X is OMe, Br, or $C_1$–$C_4$ alkyl, M is $C_1$–$C_4$ alkyl, Br, Cl, or O($C_1$–$C_4$ alkyl); and L is CH, or N.

X. The invention also encompasses use of aminothiazole derivatives of the following formula, disclosed in WO 97/00868:

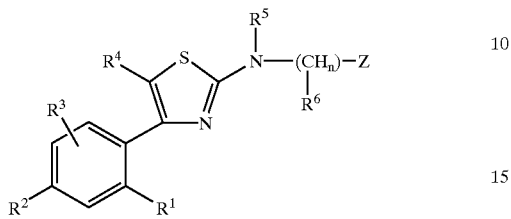

wherein each of $R^1$ and $R^2$ is independently a halogen atom; a $C_1$–$C_5$ hydroxyalkyl radical; $C_1$–$C_5$ alkyl; $C_7$–$C_{10}$ aralkyl; $C_1$–$C_5$ alkoxy; trifluoromethyl; nitro; nitrile; a group —SR where R is hydrogen, a $C_1$–$C_5$ alkyl radical or a $C_7$–$C_{10}$ aralkyl radical; a group S—CO—R where R is a $C_1$–$C_5$ alkyl radical or aralkyl in which the aryl portion is $C_6$–$C_8$ and the alkyl portion is $C_1$–$C_4$; a group —COOR' where R' is hydrogen or $C_1$–$C_5$ alkyl; a group —CONR'R" where R' and R" are as defined above for R'; a group —NR'R" where R' and R" are as previously defined for R'; a group —CONRaRb or NRaRb, where Ra and Rb, taken together with the nitrogen atom to which they are attached, form a 5 to 7-membered heterocyclic ring; or a group —NHCO—NR'R", where R' and R" are as defined above for R'; $R^3$ is hydrogen or as defined for $R^1$ and $R^2$ is a hydrogen atom; $C_{1-5}$ alkyl; halogen; a hydroxymethyl group; or a formyl group; $R^5$ is $C_1$–$C_5$ alkyl; a $C_3$–$C_7$ cycloalkyl group; a cycloalkylalkyl group in which the cycloalkyl portion is $C_3$–$C_7$ and the alkyl portion is $C_1$–$C_5$; or $C_5$–$C_6$ alkenyl; n is 0 or 1; $R^5$ is $C_1$–$C_5$ alkyl; alkoxyalkyl in which the alkyl portions are $C_1$–$C_5$; $C_3$–$C_7$ cycloalkyl; a cycloalkylalkyl group in which the cycloalkyl portion is $C_3$–$C_7$ and the alkyl portion is $C_1$–$C_5$; a cycloalkyloxyalkyl radical in which the cycloalkyl is $C_3$–$C_7$ and the alkyl is $C_1$–$C_4$; a hydroxyalkyloxyalkyl radical in which the alkyls are $C_2$–$C_{10}$; or an alkoxyalkyloxyalkyl radical in which the alkyls are $C_3$–$C_{12}$; and Z is an optionally substituted bi- or tricyclic aromatic or heteroaromatic group; and stereoisomers and/or addition salts thereof.

XI. CRF antagonists of the following formula, disclosed in WO 97/29109, may also be employed:

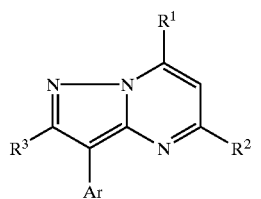

including the stereoisomers and the pharmaceutically acceptable acid addition salt forms thereof, wherein R' is $NR^4R^5$ or $OR^5$;

$R^2$ is $C_1$–$C_6$alkyl, $C_1$–$C_6$alkyloxy or $C_1$–$C_6$alkylthio, $R^3$ is hydrogen, $C_1$–$C_6$alkyl, $C_1$–$C_6$alkylsulfonyl, $C_1$–$C_6$alkylsulfoxy or $C_1$–$C_6$alkylthio;

$R^4$ is hydrogen, $C_1$–$C_6$alkyl, mono- or di($C_3$–$C_6$cyloalkylmethyl, $C_3$–$C_6$cyloalkyl, $C_3$–$C_6$alkenyl, hydroxyC_1–C_6alkyl, $C_1$–$C_6$akylcarbonyloxyC_1–C_6alkyl or $C_1$–$C_6$alkyloxyC_1–C_6alkyl;

$R^5$ is $C_1$–$C_8$alkyl, mono- or di($C_3$–$C_6$cycloalkyl)methyl, $Ar^1CH_2$, $C_3$–$C_6$alkenyl, $C_1$–$C_6$alkyloxyC_1–C_6alkyl, hydroxyC_1–C_6alkyl, thienylmethyl, furanylmethyl, $C_1$–$C_6$alkylthioC_1–C_6alkyl, morpholinyl, mono- or di($C_1$–$C_6$alkyl)aminoC_{1-6}alkyl, di($C_1$–$C_6$alkyl)amino, $C_1$–$C_6$alkylcarbonylC_1–C_6alkyl, $C_1$–$C_6$alkyl substituted with imidazolyl; or a radical of formula —Alk-O—CO—$Ar^1$;

or $R^4$ and $R^5$ taken together with the nitrogen atom to which they are attached may form a pyrrolidinyl, piperidinyl, homopiperidinyl or morpholinyl group, optionally substituted with $C_1$–$C_6$alkyl or $C_1$–$C_6$alkyloxyC_1–C_6alkyl; and Ar is phenyl; phenyl substituted with 1, 2 or 3 substituents independently selected from halo, $C_1$–$C_6$alkyl, trifluoromethyl, hydroxy, cyano, $C_1$–$C_6$alkyloxy, benzyloxy, $C_1$–$C_6$alkylthio, nitro, amino and mono- or di($C_1$–$C_6$alkyl)amino; pyridinyl; pyridinyl substituted with 1–2 or 3 substituents independently selected from halo, $C_1$–$C_6$alkyl, trifluoromethyl, hydroxy, cyano, $C_1$–$C_6$alkyloxy, benzyloxy, $C_1$–$C_6$alkylthio, nitro, amino, mono- or di($C_1$–$C_6$alkyl)amino and piperidinyl; and wherein said substituted phenyl may optionally be further substituted with one or more halogens;

$Ar^1$ is phenyl; phenyl substituted with 1, 2 or 3 substituents each independently selected from halo, $C_1$–$C_6$alkyl, $C_1$–$C_6$alkyloxy, di($C_1$–$C_6$alkyl) aminoC_1–C_6alkyl, trifluoromethyl and $C_1$–$C_6$alkyl substituted with morpholinyl; or pyridinyl; and Alk is $C_1$–$C_6$alkanediyl; with the proviso that 5-methyl-3-phenyl-7-(phenylmethoxy)-pyrazolo[1,5-a]-pyrimidine and 2,5-dimethyl-7-(methylamino)-3-phenyl-pyrazolo[1,5-a]pyrimidine are not included.

Preferred compounds of this formula are those wherein $R^2$ is methyl; $R^3$ is hydrogen, or $C_1$–$C_6$ alkyl; and Ar is substituted phenyl or 3-pyridyl.

XII. CRF antagonists of the following formula, disclosed in WO 97/29110, may also be employed:

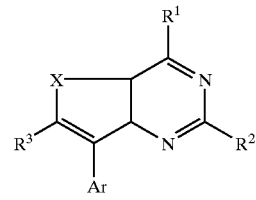

including the stereoisomers and the pharmaceutically acceptable acid addition salt forms thereof, wherein X is S, SO or $SO_2$;

$R^1$ is $NR^4R^5$ or $OR^5$;

$R^2$ is $C_1$–$C_6$alkyl, $C_1$–$C_6$alkyloxy or $C_1$–$C_6$alkylthio;

$R^3$ is hydrogen, $C_1$–$C_6$alkyl, $C_1$–$C_6$alkylsulfonyl, $C_1$–$C_6$alkylsulfoxy or $C_1$–$C_6$alkylthio;

$R^4$ is hydrogen, $C_1$6alkyl, mono- or di($C_3$–$C_6$cycloalkyl)methyl, $C_3$–$C_6$cycloalkyl, $C_3$–$C_6$alkenyl, hydroxyC_1–C_6alkyl, $C_1$–$C_6$alkylcarbonyloxyC_1–C_6alkyl or $C_1$–$C_6$alkyloxyC_1–C_6alkyl;

$R^5$ is $C_1$–$C_8$alkyl, mono- or di($C_3$–$C_6$cycloalkyl)methyl, $Ar^1CH_2$, $C_3$–$C_6$alkenyl, $C_1$–$C_6$alkyloxyC_1–C_6alkyl, hydroxyC_1–C_6alkyl, thienylmethyl, furanylmethyl, C$_1$–C$_6$alkylthioC$_1$–C$_6$alkyl, morpholinyl, mono- or di(C$_1$–C$_6$alkyl)aminoC$_1$–C$_6$alkyl, di(C$_1$–C$_6$alkyl)amino, C$_1$–C$_6$alkylcarbonylC$_1$–C$_6$alkyl, C$_1$–C$_6$alkyl substituted with imidazolyl; or a radical of formula -Alk-O—CO—Ar I; or R$^4$ and R$^5$ taken together with the nitrogen atom to which they are attached may form a pyrrolidinyl, piperidinyl, homopiperidinyl or morpholinyl group, optionally substituted with C$_1$–C$_6$alkyl or C$_1$–C$_6$alkyloxyC$_1$–C$_6$alkyl;

Ar is phenyl; phenyl substituted with 1, 2 or 3 substituents independently selected from halo, C$_1$–C$_6$alkyl, trifluoromethyl, hydroxy, cyano, C$_1$–C$_6$alkyloxy, benzyloxy, C$_1$–C$_6$alkylthio, nitro, amino and mono- or di(C$_1$–C$_6$alkyl)amino; pyridinyl; pyridinyl substituted with 1, 2 or 3 substituents independently selected from halo, C$_1$–C$_6$alkyl, trifluoromethyl, hydroxy, cyano, C$_1$–C$_6$alkyloxy, benzyloxy, C$_1$–C$_6$alkylthio, nitro, amino, mono- or di(C$_1$–C$_6$alkyl)amino and piperidinyl; and wherein said substituted phenyl may optionally be further substituted with one or more halogens;

Ar$^1$ is phenyl; phenyl substituted with 1, 2 or 3 substituents each independently selected from halo, C$_1$–C$_6$alkyl, C$_1$–C$_6$alkyloxy, di(C$_1$–C$_6$alkyl)aminoC$_1$–C$_6$alkyl trifluoromethyl, and C$_1$–C$_6$alkyl substituted with morpholinyl; or pyridinyl; and Alk is C$_1$–C$_6$alkanediyl.

Preferred compounds of this group include those wherein:
i) R$^2$ is methyl;
ii) R$^2$ is methyl; and Ar is substituted phenyl or 3-pyridyl;
iii) R$^2$ is methyl; R$^3$ is methyl; and Ar is substituted phenyl or 3-pyridyl.

Specific CRF antagonists useful in the practice of the invention, include, without limitation, the following compounds:

4-(1-ethyl-propoxy)-3,6-dimethyl-2-(2,4,6-trimethylphenoxy)-pyridine;
butyl-[2,5-dimethyl-7-(2,4,6-trimethylphenyl)-6,7dihydro-5H-pyrrolo[2,3-d]pyrimidin-4-yl]-ethylamino;
4-(butyl-ethylamino)-2,5-dimethyl-7-(2,4,6-trimethylphenyl)-5,7-dihydro-pyrrolo[2,3-d]pyrimidin-6-one;
4-(1-ethylpropoxy)-2,5-dimethyl-6-(2,4,6-trimethylphenoxy)-pyrimidine;
N-butyl-N-ethyl-2,5-dimethyl-NN-(2,4,6-trimethylphenylypyrimidine-4,6-diamine;
[4-(1-ethyl-propoxy)-3,6-dimethyl-pyridin-2-yl]-(2,4,6-trimethylphenyl)-amine;
6-(ethyl-propyl-amino)-2,7-dimethyl-9-(2,4,6-trimethylphenyl)-7,9-dihydro-purin-8-one;
3{(4-methyl-benzyl)-[3,6-dimethyl-1-(2,4,6-trimethylphenyl)-1H-pyrazolo[3,4-d]pyrimidin-4-yl]-amino}-propan-1-ol;
diethyl-[6-methyl-3-methylsulfanyl-1-(2,4,6-trichlorophenyl)-1H-pyrazolo[3,4-d]pyrimidin-4-yl]-amine;
2-{butyl-[6-methyl-3-methylsulfanyl-1-(2,4,6-trichlorophenyl)-1H-pyrazolo[3,4-d]pyrimidin-4-yl]-amino}-ethanol;
dibutyl-[6-methyl-3-methylsulfanyl-1-(2,4,6-trichlorophenyl)-1H-pyrazolo[3,4-d]pyrimidin-4-yl}amine;
butyl-ethyl-[6-methyl-3-methylsulfanyl-1-(2,4,6-trichlorophenyl)-1H-pyrazolo[3,4-d]pyrimidin4-yl]-amine;
butyl-ethyl-[6-methyl-3-methylsulfonyl-1-(2,4,6-trichlorophenyl)-1H-pyrazolo[3,4-d]pyrimidin4-yl]-amine;
butyl-cyclopropylmethyl-[6-methyl-3-methylsulfanyl-1-(2,4,6-trichlorophenyl)-1H-pyrazolo[3,4-d]pyrimidin-4-yl]-amine;
di-1-propyl-[6-methyl-3-methylsulfanyl-1-(2,4,6-trichlorophenyl)-1H-pyrazolo[3,4-d]pyrimidin-4-yl]-amine;
diallyl-[6-methyl-3-methylsulfanyl-1-(2,4,6-trichlorophenyl)-1H-pyrazolo[3,4-d]pyrimidin-4-yl]-amine;
butyl-ethyl-[6-chloro-3-methylsulfanyl-1-(2,4,6-trichlorophenyl)-1H-pyrazolo[3,4-d]pyrimidin-4-yl]-amine;
butyl-ethyl-[6-methoxy-3-methylsulfanyl-1-(2,4,6-trichlorophenyl 1H-pyrazolo[3,4-d]pyrimidin-4-yl]-amine;
propyl-ethyl-[3,6-dimethyl-1-(2,4,6-trimethylphenyl)-1H-pyrazolo[3,4-d]pyrimidin-4-yl]-amine;
4-(1-ethyl-propyl)-6-methyl-3-methylsulfanyl-1-(2,4,6-trimethylphenyl)-1H-pyrazolo[3,4-d]pyrimidine;
n-butyl-ethyl-(2,5-dimethyl-7-(2,4,6-trimethylphenyl7H-pyrrolo[2,3-d]pyrimidin4-yl]amine;
di-n-propyl-[2,5-dimethyl-7-(2,4,6-trimethylphenyl)-7H-pyrrolo[2,3]pyrimidin-4-yl]amine;
ethyl-n-propyl-[2,5-dimethyl-7-(2,4,6-trimethylphenyl)-7H-pyrrolo[2,3-d]pyrimidin-4-yl]amine;
diethyl-2,5-dimethyl-7-(2,4,6-trimethylphenyl)-7H-pyrrolo[2,3-d]pyrimidin-4-yl]amine;
n-butyl-ethyl-[2,5,6-trimethyl-7-(2,4,6-trimethylphenyl)-7H-pyrrolo[2,3-d]pyrimidin-4-yl]amine;
2-{N-n-butyl-N-[2,5-dimethyl-7-(2,4,6-trimethylphenyl)-7H-pyrrolo[2,3-d]pyrimidin4-yl]amino}-ethanol;
4-(1-ethyl-propyl)-2,5,6-trimethyl-7-(2,4,6-trimethylphenyl)-7H-pyrrolo[2,3-d]pyrimidine;
n-butyl-ethyl-[2,5-dimethyl-7-(2,4-dimethylphenyl)-7H-pyrrolo[2,3-d]pyrimidin-4-yl]amine;
2,5-dimethyl-7-(2,4,6-trimethylphenyl)-7H-pyrrolo[2,3-d]pyrimidyl-4-yl]-(1-ethyl-propyl)amine;
butyl-[3,6-dimethyl-1-(2,4,6-trimethylphenyl)-1H-pyrazolo[3,4-b]pyridin-4-yl]thylamine;
[3,6-dimethyl-1-(2,4,6-trimethylphenyl)-1H-pyrazolo[3,4,b]pyridin-4-yl]-(1-methoxymethylpropyly)-amine;
4-(1-methoxymethylpropoxy)-3,6-dimethyl-1-(2,4,6-trimethylphenyl)-1H-pyrazolo[3,4-b]pyridine;
(1-ethylpropyl)-[3,5,6-trimethyl-1-(2,4,6-trimethylphenyl)-1H-pyrazolo[3,4-b]pyridin-4-yl]-amine;
4-(1-ethylpropoxy)-2,5-dimethyl-7-(2,4,6-trimethylphenyl)-7H-pyrrolo[2,3-b]pyridine;
4-(1-ethylpropoxy)-2,5,6-trimethyl-7-(2,4,6-trimethylphenyl)-7H-pyrrolo[2,3-b]pyridine;
4-(1-ethylpropoxy)-2,5-dimethyl-7-(2,6-dimethyl-4-bromophenyl)-7H-pyrrolo[2,3-b]pyridine;
2,5,6-trimethyl-7-(1-propylbutyl)-4-(2,4,6-trimethylphenoxy)-7H-pyrrolo[2,3-d]pyrimidine;
1-(1-ethylpropyl)-6-methyl4-(2,4,6-trimethylphenylamino)-1,3-dihydro-imidazo[4,5-c]pyridin-2-one;
9-(1-ethylpropyl)-2-methyl-6-(2,4,6-trimethylphenylamino)-7,9-dihydro-purin-8-one;

1-(1-ethylpropyl)-6-methyl-4-(2,4,6-trimethylphenoxy)-1,3-dihydro-imidazo[4,5-c]pyridin-2-one;

1-(1-ethylpropyl)-6-methyl-4-(2,4,6-trimethylphenoxy)-1H-imidazo[4,5-c]pyridine;

1-(1-ethylpropyl)-3,6-dimethyl-4-(2,4,6-trimethylphenoxy)-1,3-dihydro-imidazo[4,5-c]pyridin-2-one;

1-(1-ethylpropyl)-3,6-dimethyl-4-(2,4,6-trimethylphenylamino)-1,3-dihydro-imidazo[4,5-c]pyridin-2-one;

1-(1-ethyl-propyl)-4,7-dimethyl-5-(2,4,6-trimethylphenoxy)-1,4-dihydro-2H-pyrido[3,4-b]pyrazin-3-one;

1-(1-ethyl-propyl)-4,7-dimethyl-5-(2,4,6-trimethylphenoxy)-1,4-dihydro-2H-pyrido[3,4-b]pyrazin-3-one;

1-(1-ethyl-propyl)-4,7-dimethyl-5-(2,4,6-trimethylphenoxy)-1,2,3,4-tetrahydro-pyrido[3,4-b]pyrazine;

1-(1-ethyl-propyl)-7-methyl-5-(2,4,6-trimethylphenoxy)-1,2,3,4-tetrahydro-pyrido[3,4-b]pyrazine;

1-(1-ethyl-propyl)-7-methyl-2oxo-5-(2,4,6-trimethylphenoxy)1,2,3,4-tetrahydro-[1,6]naphthyridine-3-carboxylic acid methyl ester;

1-(1-ethyl-propyl)-7-methyl-2-oxo-5-(2,4,6-trimethylphenoxy1,2,3,4-tetrahydro-[1,6naphthyridine-3-carboxylic acid isopropyl ester;

1-(1-ethyl-propyl)-7-methyl-5-(2,4,6-trimethylphenoxy)-3,4-dihydro-1H-[1,6]naphthyridin-2-one;

1-(1-ethyl-propyl7-methyl-5-(2,4,6-trimethyl-phenoxy)-1,2,3,4-tetrahydro-[1,6]naphthyridine;

1-(1-ethyl-propyl)-7-methyl-5-(2,4,6-trimethyl-phenoxy)-1,4-dihydro-2H-3-oxa-1,6-diaza-naphthalene;

1-(1-ethyl-propyl)4,7-dimethyl-5-(2,4,6trimethyl-phenoxy)-1,4-dihydro-2H-3-oxa-1,6-diaza-naphthalene;

1-(1-ethyl-propyl)-3,7-dimethyl-5-(2,4,6-trimethyl-phenoxy)-3,4-dihydro-1H-3-oxa-[1,6]-naphthyridin-2-one;

1-(1-ethyl-propyl)-3,3,6-trimethyl-4-(2,4,6-trimethyl-phenoxy)-2,3-dihydro-1H-pyrrolo[3,2-c]pyridine;

7-(1-ethyl-propoxy)-5-methyl-3-(2,4,6-trimethyl-phenyl)-pyrazolo[1,5-a]pyrimidine;

[2,5-dimethyl-3-(2,4,6-trimethyl-phenyl)-pyrazolo[1,5-a]pyrimidin-7-yl]-(1-ethyl-propyl)-amine;

(1-ethyl-propyl)-(5-methyl-3-(2,4,6-trimethyl-phenyl)-pyrazolo[1,5-a]pyrimidin-7-yl]-amine;

7-(1-ethyl-propoxy)-2,5-dimethyl-3-(2,4,6-trimethyl-phenyl)-pyrazolo[1,5-a]pyrimidine;

[2,5-dimethyl-3-(2,4,6-trimethyl-phenyl)-pyrazolo[1,5-a]pyrimidin-7-yl]-ethyl-propyl-amine;

[6-bromo-5-bromomethyl-3-(2,4,6-trimethyl-phenyl)-3H-[1,2,3]triazolo[4,5-b]pyridin-7yl]-(1-ethyl-propyl)-amine;

(1-ethyl-propyl)-[5methyl-3-(2,4,6-trimethyl-phenyl)-3H-[1,2,3]triazolo[4,5-b]pyridin-7-yl]-amine;

[6-bromo-5-methyl-3-(2,4,6-trimethyl-phenyl)-3H-[1,2,3]triazolo[4,5-b]pyridin-7-yl]-ethyl-propyl)-methyl-amine;

7-(1-ethyl-propoxy)-5-methyl-3-(2,4,6-trimethyl-phenyl)-3H-[1,2,3]triazolo[4,5-b]pyridine;

4-(1-ethyl-propoxy)-2,5-dimethyl-7-(2,4,6-trimethyl-phenyl)-5H-pyrrolo[3,2-d]pyrimidine;

(±)-2,5-dimethyl4-(tetrahydro-furan-3-yloxy)-7-(2,4,6-trimethyl-phenyl)-5H-pyrrolo-[3,2-d]pyrimidine;

2,5-dimethyl4-(S)-(tetrahydro-furan-3-yloxy)-7-(2,4,6-trimethyl-phenyl)-5H-pyrrolo-[3,2-d]pyrimidine;

2,5-dimethyl4-(1-propyl-butoxy)-7-(2,4,6-trimethyl-phenyl)-5H-pyrrolo[3,2-dipyrimidine;

4-sec-butylsulfanyl-2,5-dimethyl-7-(2,4,6-trimethyl-phenyl)5H-pyrrolo[3,2-d]pyrimidine;

4-(butyl-ethyl-amino)-2,6-dimethyl-8-(2,4,6-trimethyl-phenyl)-5,8-dihydro-6H-pyrido[2,3-d]pyrimidin-7-one;

8-(1-ethyl-propoxy)-6-methyl-4-(2,4,6-trimethyl-phenyl)-3,4-dihydro-H-pyrido[2,3-b]pyrazin-2-one;

8-(1-ethyl-propoxy)-6-methyl-4-(2,4,6-trimethyl-phenyl)-1,2,3,4-tetrahydro-pyrido[2,3-b]pyrazine;

4-(1-ethyl-propoxy)-2-methyl-8-(2,4,6-trimethyl-phenyl)-quinoline;

5-(1-ethyl-propoxy)-7-methyl-1-(2,4,6-trimethyl-phenyl)-1,4-dihydro-2H-3-oxa-1,8-diaza-naphthalene;

5-(1-ethyl-propoxy)-7-methyl-1-(2,4,6-trimethyl-phenyl)-1,2-dihydro-3-oxa-1,8-diaza-naphthalen-4-one;

8-(1-ethyl-propoxy)-1,6-dimethyl-4-(2,4,6-trimethyl-phenyl)-1,2,3,4-tetrahydro-pyrido[2,3-b]pyrazine;

(1-ethyl-propyl)-[2-methyl-8-(2,4,6-trimethyl-phenyl)quinolin-4-yl]-amine;

4-(butyl-ethyl-amino)-2,6-dimethyl-8-(2,6-dimethyl-4-bromo-phenyl)-5,8-dihydro-6H-pyrido[2,3-d]pyrimidin-7-one;

4-(butyl-ethyl-amino)-2-methyl-8-(2,6-dimethyl-4-bromo-phenyl)-5,8-dihydro-6H-pyrido[2,3-d]pyrimidin-7-one;

4-(1-ethyl-propoxy)-2-methyl-8-(2,6-dimethyl-4-bromo-phenyl)-5,8-dihydro-6H-pyrido[2,3-d]pyrimidin-7-one;

(butyl-ethyl)-(2-methyl-8-(2,6-dimethyl-4-bromo-phenyl)-5,6,7,8-tetrahydro-pyrido[2,3-d]pyrimidin-4-yl]-amine;

(propyl-ethyl)-(2-methyl-8-(2,6-dimethyl-4-bromo-phenyl)-5,6,7,8-tetrahydro-pyrido[2,3-d]pyrimidin-4-yl)-amine;

(diethyl [2-methyl-8-(2,6-dimethyl-4-bromo-phenyl)-5,6,7,8-tetrahydro-pyrido[2,3-d]pyrimidin-4-yl]-amine;

(1-ethyl-propyl)-[2-methyl-8-(2,6-dimethyl-4-bromo-phenyl)-5,6,7,8-tetrahydro-pyrido[2,3-d]pyrimidin-4-yl]-amine;

(1-ethyl-propoxy)-2-methyl-8-(2,6-dimethyl-4-bromo-phenyl)-5,6,7,8-tetrahydro-pyrido[2,3-d]pyrimidine;

4-(butyl-ethyl-amino)-2-methyl-8-(2,4,6-trimethyl-phenyl)-5,8-dihydro-6H-pyrido[2,3-d]pyrimidin-7-one;

4-(1-ethyl-propoxy)-2-methyl-8-(2,4,6-trimethyl-phenyl)-5,8-dihydro-6H-pyrido[2,3-d]pyrimidin-7-one;

(butyl-ethyl)-[2-methyl-8-(2,4,6-trimethyl-phenyl)-5,6,7,8-tetrahydro-pyrido[2,3-d]pyrimidin-4-yl]-amine;

(propyl-ethyl)-[2-methyl-8-(2,4,6-trimethyl-phenyl)-5,6,7,8-tetrahydro-pyrido[2,3-d]pyrimidin-4-yl]-amine;

(diethyl)-[2-methyl-8-(2,4,6-trimethyl-phenyl)-5,6,7,8-tetrahydro-pyrido[2,3-d]pyrimidin-4-yl]-amine;

(1-ethyl-propyl)-[2-methyl-8-(2,4,6-trimethyl-phenyl-5,6,7,8-tetrahydro-pyrido[2,3-d]pyrimidin-4-yl]-amine;

(1-ethyl-propoxy)-2-methyl-8-(2,4,6-trimethyl-phenyl)-5,6,7,8-tetrahydro-pyrido[2,3-d]pyrimidine;

8-(1-ethyl-propoxy)-6-methyl-4-(2,6-dimethyl-4-bromo-phenyl)-3,4-dihydro-1H-pyrido [2,3-b]pyrazin-2-one;

8-(1-ethyl-propoxy)-6-methyl-4-(2,6-dimethyl-4-bromo-phenyl)-1,2,3,4-tetrahydro-pyrido[2,3-b]pyrazine;

4-(1-ethyl-propoxy)-2-methyl-8-(2,6-dimethyl-4-bromo-phenyl)-quinoline;

5-(1-ethyl-propoxy)-7-methyl-1-(2,6-dimethyl-4-bromo-phenyl)-1,4-dihydro-2H-3-oxa-1,8-diaza-naphthalene;

5-(1-ethyl-propoxy)-7-methyl-1-(2,6-dimethyl-4-bromo-phenyl)-1,2-dihydro-3-oxa-1,8-diaza-naphthalen-4-one;

8-(1-ethyl-propoxy)-1,6-dimethyl-4-(2,6-dimethyl-4-bromo-phenyl)-1,2,3,4- tetrahydro-pyrido[2,3-b]pyrazine;

(1-ethyl-propyl)-[2-methyl-8-(2,6-dimethyl-4-bromo-phenyl)-quinolin-4-yl]-amine;

4-(butyl-ethyl-amino)-2,6-dimethyl-8-(2,6-dimethyl-4-chloro-phenyl)-5,8-dihydro-6H-pyrido[2,3-d]pyrimidin-7-one;

8-(1-ethyl-propoxy)-6-methyl-4-(2,6-dimethyl-4-chloro-phenyl)-3,4-dihydro-1H-pyrido[2,3-b]pyrazin-2-one;

8-(1-ethyl-propoxy)-6-methyl-4-(2,6-dimethyl-4-chloro-phenyl)-1,2,3,4-tetrahydro-pyrido[2,3-b]pyrazine;

4-(1-ethyl-propoxy)-2-methyl-8-(2,6-dimethyl-4-chloro-phenyl)-quinoline;

5-(1-ethyl-propoxy)-7-methyl-1-(2,6-dimethyl-4-chloro-phenyl)-1,4-dihydro-2H-3-oxa-1,8-diaza-naphthalene;

5-(1-ethyl-propoxy)-7-methyl-1-(2,6-dimethyl-4-chloro-phenyl)-1,2-dihydro-3-oxa-1,8-diaza-naphthalen-4-one;

8-(1-ethyl-propoxy)-1,6-dimethyl-4-(2,6-dimethyl-4-chloro-phenyl)-1,2,3,4-tetrahydro-pyrido[2,3-b]pyrazine;

(1-ethyl-propyl)-[2-methyl-8-(2,6-dimethyl-4-chloro-phenyl)-quinolin-4-yl]-amine 8-(1-hydroxymethyl-propoxy)-6-methyl-4-(2,4,6-trimethyl-phenyl)-3,4-dihydro-1H-pyrido[2,3-b]pyrazin-2-one;

8-(1-hydroxymethyl-propyl)-6-methyl-4-(2,4,6-trimethyl-phenyl)-3,4-dihydro-1H-pyrido[2,3-b]pyrazin-2-one;

8-(1-ethyl-propyl)-6-methyl-4-(2,4,6-trimethyl-phenyl)-3,4-dihydro-1H-pyrido[2,3-b]pyrazin-2-one;

8-diethylamino-6-methyl-4-(2,4,6-trimethyl-phenyl)-3,4-dihydro-1H-pyrido[2,3-b]pyrazin-2-one;

8-(ethyl-propyl-amino)-6-methyl-4-(2,4,6-trimethyl-phenyl)-3,4-dihydro-1H-pyrido[2,3-b]pyrazin-2-one;

8-(butyl-ethyl-amino)-6-methyl-4-(2,4,6-trimethyl-phenyl)-3,4-dihydro-1H-pyrido [2,3-b]pyrazin-2-one;

8-(1-hydroxymethyl-propoxy)-6-methyl-4-(2,4,6-trimethyl-phenyl)-1,2,3,4-tetrahydro-pyrido[2,3-b]pyrazine;

8-(1-hydroxymethyl-propyl)-6-methyl-4-(2,4,6-trimethyl-phenyl)-1,2,3,4-tetrahydro-pyrido[2,3-b]pyrazine;

8-(1-ethyl-propyl)-6-methyl-4-(2,4,6-trimethyl-phenyl)-1,2,3,4-tetrahydro-pyrido[2,3-b]pyrazine;

8-diethylamino-6-methyl-4-(2,4,6-trimethyl-phenyl)-1,2,3,4-tetrahydro-pyrido[2,3-b]pyrazine;

8-(ethyl-propyl-amino)-6-methyl-4-(2,4,6-trimethyl-phenyl)-1,2,3,4-tetrahydro-pyrido[2,3-b]pyrazine;

8-(butyl-ethyl-amino)-6-methyl-4-(2,4,6-trimethyl-phenyl)-1,2,3,4-tetrahydro-pyrido[2,3-b]pyrazine;

4-(1-hydroxymethyl-propoxy)-2-methyl-8-(2,4,6-trimethyl-phenyl)-quinoline;

4-(1-hydroxymethyl-propyl)-2-methyl-8-(2,4,6-trimethyl-phenyl)-quinoline;

4-(1-ethyl-propyl)-2-methyl-8-(2,4,6-trimethyl-phenyl)-quinoline;

4-diethylamino-2-methyl-8-(2,4,6-trimethyl-phenyl)-quinoline;

4-(ethyl-propyl-amino)-2-methyl-8-(2,4,6-trimethyl-phenyl)-quinoline;

4-(butyl-ethyl-amino)-2-methyl-8-(2,4,6-trimethyl-phenyl)-quinoline;

5-(1-hydroxymethyl-propoxy)-7-methyl-1-(2,4,6-trimethyl-phenyl)-1,4-dihydro-2H-3-oxa-1,8-diaza-naphthalene;

5-(1-hydroxymethyl-propyl)-7-methyl-1-(2,4,6-trimethyl-phenyl)-1,4-dihydro-2H-3-oxa-1,8-diaza-naphthalene;

5-(1-ethyl-propyl)-7-methyl-1-(2,4,6-trimethyl-phenyl)-1,4-dihydro-2H-3-oxa-1,8-diaza-naphthalene;

5-diethylamino-5-methyl-1-(2,4,6-trimethyl-phenyl)-1,4-dihydro-2H-3-oxa-1,8-diaza-naphthalene;

5-(ethyl-propyl-amino)-7-methyl-1-(2,4,6-trimethyl-phenyl)-1,4-dihydro-2H-3-oxa-1,8-diaza-naphthalene;

8-(butyl-ethyl-amino)-6-methyl-4-(2,4,6-trimethyl-phenyl)-1,4-dihydro-2H-3-oxa-1,8-diaza-naphthalene;

4-(2,4-dichlorophenyl)-5-methyl-2-[N-(1-(methoxymethyl)-1-(naphth-2-yl)methyl)-N-propyl]thiazole;

oxalate of 4-(2,4-dicholorphenyl)-5-methyl-2-[N-6-methoxyisoquinol-5-yl)-N-propyl]thiazole;

oxalate of 4-2-chloro-4-methoxyphenyl)-5-methyl-2-[N-(6-methoxyisoquinol-5yl)-N-propamino]thiazole;

4-(2-chloro-4-methoxyphenyl)-5-methyl-2-[N-1-methoxynaphth-2-yl)-N-propyl]thiazole;

oxalate of 4-(2-chloro-4-methoxyphenyl)-5-methyl-2-[N-(6-methoxyisoquinol-5-yl)-N-propyl]thiazole;

oxalate of 4-(2-chloro-4-methoxyphenyl)-5-methyl-2-[N-6-chloroisoquinol-5-yl)-N-(6-methoxyisoquinol-5-yl)-N-propyl]thiazole;

4-(2-chloro-4-methoxyphenyl)-5-methyl-2-[N-(1-methoxynaphth-2-yl)-N-propyl]thiazole;

oxalate of 4-(2-chloro-4-trifluoromethylphenyl)-5-methyl-2-[N-6-methoxylsoquinol-5-yl)-N-propyl]thiazole;

chlorohydrate of a 4-chloro-4-methoxyphenyl)-5-methyl-2-[N-2-ethoxynaphth-1yl)-N-propyl]thiazole;

chlorhydrate of 4-(2-chloro-4-methoxyphenyl)-5-methyl-2[N-(2,3-dimethylnaphth-1-yl)-N-propyl]thiazole;

chlorhydrate de 4-(2-chloro-4-methoxyphenyl)-5-methyl-2-[N-(6-bromo-2-methoxynaphth-1-yl)-N-propyl]thiazole;

chlorhydrate of 4-(2-chloro-4-methoxyphenyl)-5-methyl-2-[N-(2,6-dimethylnaphth-1-yl)-N-propyl]thiazole;

chlorhydrate of 4-(2-chloro-4-methoxyphenyl)-5-methyl-2-[N-(1-(methoxymethyl)-1-(naphth-2-yl)methyl)-N-propyl]thiazole;

chlorhydrate of 4-(2-chloro-4-methoxyphenyl)-5-methyl-2-[N-(1-(cyclopropyl)-1-(naphth-2-yl)methyl)-N-propyl]thiazole;

3-(2,4-dichlorophenyl)-5-methyl-7(N-propyl-N-cyclopropanemethylamino)-pyrazolo[2,3-a]pyrimidine;

3-(2,4-dichlorophenyl)-5-methyl-7-(N-allyl-N-cyclopropanemethylamino)-pyrazolo[2,3-a]pyrimidine;

2-methylthio-3-(2,4-dichlorophenyl)-5-methyl-7-(N,N-diallylamino)-pyrazolo[2,3-a]pyrimidine;

2-methylthio-3-(2,4-dichlorophenyl)-5-methyl-7-(N-butyl-N-cyclopropanemethyl-amino)pyrazolo[2,3-a]pyrimidine;

2-methylthio-3-(2,4-dichlorophenyl)-5-methyl-7-(N-propyl-N-cyclopopanemethyl-amino) pyrazolo[2,3-a]pyrimidine;

2-methyl-3-(4-chlorophenyl)-5-methyl-7-(N,N-dipropylamino)-pyrazolo[2,3-a)pyrimidine;

3-[6-(dimethylamino)-3-pyridinyl-2,5-dimethyl-N,N-dipropylpyrazolo[2,3-a]pyrimidin-7-amine;

3-[6-(dimethylamino)-4-methyl-3-pyridinyl]-2,5-dimethyl-N,N-dipropyl-pyrazolo[2,3-a]pyrimidine-7-amine;

3-(2,4-dimethoxyphenyl)-2,5-dimethyl-7-(N-propyl-N-methyloxyethylamino)-pyrazolo(2,3-a)pyrimidine;

7-(N-diethylamino)-2,5-dimethyl-3-(2-methyl-4-methoxyphenyl-[1,5-a]-pyrazolopyrimidine;

7-(N-(3-cyanopropyl)-N-propyl-2,5, dimethyl-3-(2,4-dimethylphenyl)-[2,5-a]-pyrazolopyrimidine;

[3,6-dimethyl-2-(2,4,6-trimethyl-phenoxy)-pyridin-4-yl]-(1-ethyl-propyl)-amine;

[2-(4-chloro-2,6-dimethyl-phenoxy)-3,6-dimethyl-pyridin-4-yl]-(1-ethyl-propyl)-amine;

cyclopropylmethyl-[3-(2,4-dimethyl-phenyl)-2,5-dimethyl-pyrazolo[1,5-a]pyrimidin-7-yl]-propyl-amine;

cyclopropylmethyl-[3-(2-methyl-4-chloro-phenyl)-2,5-dimethyl-pyrazolo[1,5-a]pyrimidin-7-yl]-propyl-amine;

cyclopropylmethyl-[3-(2,4-di-chloro-phenyl)-2,5-dimethyl-pyrazolo[1,5-a]pyrimidin-7-yl]-propyl-amine, [3-(2-methyl-4-chloro-phenyl)-2,5-dimethyl-pyrazolo[1,5-a]pyrimidin-7-yl]-di-propyl-amine;

[2,5-dimethyl-3-(2,4-dimethyl-phenyl)-pyrazolo[1,5-a]pyrimidin-7-yl]-(1-ethyl-propyl)-amine;

[2,5-dimethyl-3-(2,4-dichloro-phenyl)-pyrazolo[1,5-a]pyrimidin-7-yl]-(1-ethyl-propyl)-amine; and 4-(1-Ethyl-propyl)-6-methyl-2-(2,4,6-trimethyl-phenoxy)-nicotinic acid methyl ester.

Methods for making the CRF antagonists described above are disclosed in the above-listed patents and published patent applications incorporated by reference herein.

In an alternative embodiment, the present invention relates to a pharmaceutical composition for the treatment of a condition selected from the group consisting of:

a) abnormal circadian rhythm; and b) depression.

The composition comprises an amount of a CRF antagonist effective to treat the condition in combination with a pharmaceutically acceptable carrier. Where the condition is depression, it is also treated with a second compound for treating depression, the second compound having an onset of action that is delayed with respect to that of the CRF antagonist.

In another aspect, the present invention relates to a method for treating or preventing a cardiovascular disease that involves administering a CRF antagonist, or a pharmaceutically acceptable salt, isomer, or prodrug thereof, in combination with a second, non-CRF antagonist compound for treating the disease. The second compound for treating the disease can be, for example, adenosine, alteplase, amiodarone, anagrelide, ardeparin, argatroban, atenolol, atorvastatin, benazepril, captopril, carvedilol, cerivastatin, clonidine, clopidrogrel, dalteparin, danaparoid, diltiazem, enalapril, fluvastatin, fosinopril, gemfibrozil, hydrochlorothiazide, irbesartan, lepirudin, lisinopril, lovastatin, oprelvekin, pravastatin, prazosin, quinapril, ramipril, saruplase, simvastatin, terazosin, valsartan, or verapamil.

In another aspect, the invention relates to treatment of migraine or non-migraine headache by administration of a CRF antagonist in combination with a non-CRF antagonist compound that treats such condition. For example, it is possible to administer a CRF antagonist with non-steroidal anti-inflammatory drugs (NSAIDs), such as aspirin, acetaminophen, ibuprofen, with anti-emetics, with preparations containing ergotamine such as dihydroergotamine, or with agents that modulate serotonin receptors (including those that modulate the $5HT_{1B}$, $5HT_{1D}$, $5HT_{1F}$ and $5HT_{2B}$ receptors) or that mimic the effects of serotonin. Particular agents include sumatriptan, naratriptan, zolmitriptan, rizatriptan, eletriptan, and almotriptan. Administration of these compounds is carried out using dosages and formulations that are well-known.

In another aspect, the invention relates to treatment of emesis using a CRF antagonist in combination with a non-CRF antagonist compound for treating emesis. Examples of such non-CRF antagonist compounds for treating emesis include tachykinin antagonists, including Nk1 antagonists, (such as compounds described in WO 99/24423, EP 867182, EP 980324, and WO 99/24423) and $5HT_3$ antagonists (such as metoclopramide, granisetron, dolasetron, ondansetron and tropisetron).

The emesis that is treated can be of any type, including emesis induced by pregnancy, vestibular disorder, post-operative sickness, gastrointestinal obstruction, reduced gastrointestinal motility, visceral pain, migraine, change in intercranial pressure, chemotherapy, radiation, toxins, and opioid analgesics.

The invention also encompasses combined pharmaceutical compositions containing the CRF antagonist, a non-CRF antagonist as defined above, and below, and a pharmaceutically acceptable carrier. Examples of such compositions include, without limitation:

1) a composition for treating abnormal circadian rhythm that contains effective amounts of a combination of a CRF antagonist and a non-CRF antagonist compound useful for treating abnormal circadian rhythm;

2) a composition for treating depression that contains effective amounts of a combination of a CRF antagonist and a second compound for treating depression that has a delayed effect;

3) a composition for treating or preventing a cardiovascular disease that contains effective amounts of a CRF antagonist in combination with a second, non-CRF antagonist compound for treating the disease;

4) a composition for treating migraine or non-migraine headache that contains effective amounts of a CRF antagonist in combination with a non-CRF antagonist compound that treats such condition; and 5) a composition for treating emesis that contains a CRF antagonist in combination with a non-CRF antagonist compound for treating emesis.

Combination treatments according to the invention can be administered as part of the same pharmaceutical composition, or the active agents can be administered separately as part of an appropriate dose regimen designed to obtain the benefits of the combination therapy.

Acid addition salts of the CRF antagonists and other agents employed in the invention can be prepared in a conventional manner by treating a solution or suspension of the corresponding free base with one chemical equivalent of a pharmaceutically acceptable acid. Conventional concentration or crystallization techniques can be employed to isolate the salts. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzene sulfonic, p-toluenesulfonic, and related acids.

The CRF antagonists and their pharmaceutically acceptable salts, and any second pharmaceutically active compounds, may be administered alone or in combination with pharmaceutically acceptable carriers, in either single or multiple doses. Suitable pharmaceutical carriers include inert solid diluents or fillers, sterile aqueous solutions, oils (e.g., peanut oil, sesame oil) and various organic solvents. The pharmaceutical compositions formed by combining the CRF antagonists and pharmaceutically acceptable carriers can be readily administered in a variety of dosage forms such as tablets, powders, lozenges, emulsions, oil soft gels, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, methylcellulose, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions containing the CRF antagonist or a pharmaceutically acceptable salt thereof in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

The effective dosages for the CRF antagonists employed in the methods of this invention will depend on the intended route of administration and factors such as the age and weight of the patient, as generally known to a physician. The dosages will also depend on the particular condition to be treated and will generally range from about 0.1 to about 300 mg/kg body weight of the patient per day, with administration carried out in single or divided dosages.

Methods that may be used to determine the CRF antagonist activity of the compounds employed to practice the invention are described e.g., in Endocrinology, 116, 1653–1659 (1985) and Peptides, 10, 179–188 (1985).

Methods that can be used to determine the CRF binding protein inhibiting activity of compounds employed to practice the invention are described in Brain Research, (1997), 745(1,2), 248–256. The binding activities of the CRF antagonists employed generally range from about 0.5 nanomolar to about 32 micromolar.

What is claimed is:

1. A method of treating a condition comprising administering a corticotropin releasing factor (CRF) antagonist in an amount effective to treat said condition, wherein said condition is a disorder that can be treated by altering circadian rhythm.

2. The method of claim 1 wherein said condition is selected from the group consisting of time zone change syndrome, seasonal affective disorder, irregular sleep-wake pattern, delayed sleep phase syndrome, advanced sleep phase syndrome, non-24 hour sleep wake disorder, light-induced clock resetting, REM sleep disorder, hypersomnia, parasomnia, narcolepsy, nocturnal enuresis, restless legs syndrome, sleep apnea, dysthymia and abnormal circadian rhythm associated with chronic administration and withdrawal of antidepressant agents.

3. The method of claim 1 wherein said CRF antagonist is selected from the group consisting of 4(1-ethyl-propoxy)-3,6-dimethyl-2-(2,4,6-trimethylphenoxy)-pyridine;

butyl-[2,5-dimethyl-7-(2,4,6-trimethylphenyl)-6,7-dihydro-5H-pyrrolo[2,3-d]pyrimidin-4-yl]-ethyl-amino;

4-(butyl-ethylamino)-2,5-dimethyl-7-(2,4,6-trimethylphenyl)-5,7-dihydro-pyrrolo[2,3-d]pyrimidin-6-one;

4-(1-ethylpropoxy)-2,5-dimethyl-6-(2,4,6-trimethylphenoxy)-pyrimidine;

N-butyl-N-ethyl-2,5-dimethyl-NN-(2,4,6trimethylphenyl)-pyrimidine-4,6-diamine;

[4-(1-ethyl-propoxy)-3,6dimethyl-pyridin-2-yl]-(2,4,6trimethylphenyl)-amine;

6-(ethyl-propyl-amino)-2,7-dimethyl-9-(2,4,6-trimethylphenyl)-7,9-dihydro-purin-8-one;

3-{(4-methyl-benzyl)-[3,6-dimethyl-1-(2,4,6-trimethylphenyl)-1H-pyrazolo[3,4-d]pyrimidin-4-yl]-amino}-propan-1-ol;

diethyl[6-methyl-3-methylsulfanyl-1-2,4,6-trichlorophenyl)-1H-pyrazolo[3,4-d]pyrimidin-4-yl]-amine;

2-{butyl-[6-methyl-3-methylsulfanyl-1-(2,4,6-trichlorophenyl)-1H-pyrazolo[3,4-d]pyrimidin-4-yl]-amino}ethanol;

dibutyl-[6-methyl-3-methylsulfanyl-1-(2,4,6-trichlorophenyl)-1H-pyrazolo[3,4-d]pyrimidin-4-yl)-amine;

butyl-ethyl-[6-methyl-3-methylsulfanyl-1-(2,4,6-trichlorophenyl)-1H-pyrazolo[3,4-d]pyrimidin-4-yl)-amine;

butyl-ethyl-[6-methyl-3-methylsulfonyl-1-(2,4,6-trichlorophenyl)-1H-pyrazolo[3,4-d]pyrimidin-4-yl]-amine;

butyl-cyclopropylmethyl-[6-methyl-3-methylsulfanyl-1-(2,4,6-trichlorophenyl)-1H-pyrazolo[3,4]pyrimidin-4-yl]-amine;

di-1-propyl)-6-methyl-3-methylsulfanyl-1-(2,4,6-trichlorophenyl)-1H-pyrazolo[3,4-d]pyrimidin-4-yl]-amine;

diallyl-[6-methyl-3-methylsulfanyl-1-(2,4,6-trichlorophenyl)-1H-pyrazolo[3,4-d]pyrimidin-4-yl]-amine;

butyl-ethyl-[6chloro-3-methylsulfanyl-1-(2,4,6-trichlorophenyl)-1H-pyrazolo[3,4-d]pyrimidin-4-yl]-amine;

butyl-ethyl-[6-methoxy-3-methylsulfanyl-1-(2,4,6-trichlorophenyl)-1H-pyrazolo[3,4-d]pyrimidin-4-yl]-amine;

propyl-ethyl-[3,6-dimethyl-1-(2,4,6-trimethylphenyl)-1H-pyrazolo[3,4-d]pyrimidin-4-yl]-amine;

4-(1-ethyl-propyl)-6-methyl-3-methylsulfanyl-1-(2,4,6-trimethylphenyl)-1H-pyrazolo[3,4-d]pyrimidine;

n-butyl-ethyl-(2,5-dimethyl-7-(2,4,6-trimethylphenyl)-7H-pyrrolo[2,3-d]pyrimidin-yl]amine;

di-n-propyl-[2,5-dimethyl-7-(2,4,6-trimethylphenyl)-7H-pyrrolo[2,3-d]pyrimidin-4-yl]amine ethyl-n-propyl-[2,5-dimethyl-7-(2,4,6-trimethylphenyl)-7H-pyrrolo[2,3-d]pyrimidin-4-yl]amine;

diethyl-2,5dimethyl-7-(2,4,6-trimethylphenyl)-7H-pyrrolo[2,3d]pyrimidin-4-yl]amine;

n-butyl-ethyl-[2,5,6-trimethyl-7-(2,4,6-trimethylphenyl)-7H-pyrrolo[2,3-d]pyrimidin-4-yl]amine;

2-{N-n-butyl-N-[2,5-dimethyl-7-(2,4,6-trimethylphenyl)-7H-pyrrolo[2,3-d]pyrimidin-4-yl]amino}ethanol;

4-(1-ethyl-propyl)-2,5,6-trimethyl-7-(2,4,6-trimethylphenyl)-7H-pyrrolo[2,3-d]pyrimidine;

n-butyl-ethyl-[2,5-dimethyl-7-(2,4-dimethylphenyl)-7H-pyrrolo[2,3d]pyrimidin-4-yl]amine;

2,5-dimethyl-7-(2,4,6-trimethylphenyl)-7H-pyrrolo[2,3-d]pyrimidyl-4-yl]-(1-ethyl-propyl)amine;

butyl-[3,6-dimethyl-1-(2,4,6-trimethylphenyl)-1H-pyrazolo[3,4-b]pyridin-4-yl]-ethylamine;

[3,6-dimethyl-1-(2,4,6-trimethylphenyl)-1H-pyrazolo[3,4,b]pyridin-4-yl]-(1-methoxymethylpropyl)-amine;

4-(1-methoxymethylpropoxy)-3,6-dimethyl-1-(2,4,6-trimethylphenyl)-1H-pyrazolo[3,4-b]pyridine;

(1-ethylpropyl)-[3,5,6-trimethyl-1-(2,4,6-trimethylphenyl)-1H-pyrazolo[3,4-b]pyridin-4-yl]amine;

4-(1-ethylpropoxy)-2,5-dimethyl-7-(2,4,6-trimethylphenyl)-7H-pyrrolo[2,3-b]pyridine;

4-(1-ethylpropoxy)-2,5,6-trimethyl-7-(2,4,6-trimethylphenyl)-7H-pyrrolo[2,3-b]pyridine;

4-(1-ethylpropoxy)-2,5-dimethyl-7-(2,6-dimethyl-4-bromophenyl)-7H-pyrrolo[2,3-b]pyridine;

2,5,6-trimethyl-7-(1-propylbutyl)-4-(2,4,6-trimethylphenoxy)-7H-pyrrolo[2,3]pyrimidine;

1-(1-ethylpropyl)-6-methyl-4-(2,4,6-trimethylphenylamino)-1,3-dihydro-imidazo[4,5-c]pyridin-2-one;

9-(1-ethylpropyl)-2-methyl-6-(2,4,6-trimethylphenylamino)-7,9-dihydro-purin-8-one;

1-(1-ethylpropyl)-6-methyl-4-(2,4,6-trimethylphenoxy)-1,3-dihydro-imidazo[4,5-c]pyridin-2-one;

1-(1-ethylpropyl)-6-methyl-4-(2,4,6-trimethylphenoxy)-1H-imidazo[4,5-c]pyridine;

1-(1-ethylpropyl)-3,6-dimethyl-4-(2,4,6-trimethylphenoxy)-1,3-dihydro-imidazo[4,5-c]pyridin-2-one;

1-(1-ethylpropyl)-3,6-dimethyl-4-(2,4,6-trimethylphenylamino)-1,3-dihydro-imidazo[4,5-c]pyridin-2-one;

1-(1-ethyl-propyl)-4,7-dimethyl-5-(2,4,6-trimethyl-phenoxy)-1,4-dihydro-2H-pyrido[3,4-b]pyrazin-3-one;

1-(1-ethyl-propyl)-4,7-dimethyl-5-(2,4,6-trimethyl-phenoxy)-1,4-dihydro-2H-pyrido[3,4-b]pyrazin-3-one;

1-(1-ethyl-propyl)-4,7-dimethyl-5-(2,4,6-trimethyl-phenoxy)-1,2,3,4-tetrahydro-pyrido[3,4-b]pyrazine;

1-(1-ethyl-propyl)-7-methyl-5-(2,4,6-trimethyl-phenoxy)-1,2,3,4-tetrahydro-pyrido[3,4-b]pyrazine;

1-(1-ethyl-propyl)-7-methyl-2-oxo-5-(2,4,6-trimethy-phenoxy)-1,2,3,4-tetrahydro-[1,6]naphthyridine-3-carboxylic acid methyl ester;

1-(1-ethyl-propyl)-7-methyl-2-oxo-5-(2,4,6-trimethyl-phenoxy)-1,2,3,4-tetrahydro-[1,6]nahthyridine-3-carboxylic acid isopropyl ester;

1-(1-ethyl-propyl)-7-methyl-5-(2,4,6-trimethyl-phenoxy)-3,4-dihydro-1H-[1,6]naphthyridin-2-one;

1-(1-ethyl-propyl)-7-methyl-5-(2,4,6-trimethyl-phenoxy)-1,2,3,4-tetrahydro-[1,6]naphthyridine;

1-(1-ethyl-propyl)-7-methyl-5-(2,4,6-trimethyl-phenoxy)-1,4-dihydro-2H-3-oxa-1,6-diaza-naphthalene;

1-(1-ethyl-propyl)-4,7-dimethyl-5-(2.4,6-trimethyl-phenoxy)-1,4-dihydro-2H-3-oxa-1,6-diaza-naphthalene;

1-(1-ethyl-propyl)-3,7-dimethyl-5-(2,4,6-trimethyl-phenoxy)-3,4-dihydro-1H-3-oxa-[1,6]-naphthyridin-2-one;

1-(1-ethyl-propyl)-3,3,6-trimethyl-4-(2,4,6-trimethyl-phenoxy)-2,3-dihydro-1H-pyrrolo[3,2-c]pyridine;

7-(1-ethyl-propoxy)-5-methyl-3-(2,4,6-trimethyl-phenyl)-pyrazolo[1,5-a]pyrimidine;

[2,5-dimethyl-3-(2,4,6-trimethyl-phenyl)-pyrazolo[1,5-a]pyrimidin-7-yl]-(1-ethyl-propyl)-amine;

(1-ethyl-propyl)-[5-methyl-3-(2,4,6-trimethyl-phenyl)-pyrazolo[1,5-a]pyrimidin-7-yl]-amine;

7-(1-ethyl-propoxy)-2,5-dimethyl-3-(2,4,6-trimethyl-phenyl)-pyrazolo[1,5-a]pyrimidine;

[2,5-dimethyl-3-(2,4,6-trimethyl-phenyl)-pyrazolo[1,5-a]pyrimidin-7-yl]-ethyl-propyl-amine;

[6-bromo-5-bromomethyl-3-(2,4,6-trimethyl-phenyl)-3H-[1,2,3]triazolo[4,5-b]pyridin-7-yl]-(1-ethyl-propyl)-amine;

(1-ethyl-propyl)-[5-methyl-3-(2,4,6-trimethyl-phenyl)-3H-[1,2,3]triazolo[4,5-b]pyridin7-yl]-amine;

[6-bromo-5-methyl-3-(2,4,6-trimethyl-phenyl)-3H-[1,2,3]triazolo[4,5-b]pyridin-7-yl](1-ethyl-propyl)-methyl-amine;

7-(1-ethyl-propoxy)-5-methyl-3-(2,4,6-trimethyl-phenyl)-3H-[1,2,3]triazolo[4,5-b]pyridine;

4-(1-ethyl-propoxy)-2,5-dimethyl-7-(2,4,6-trimethyl-phenyl)-5H-pyrrolo[3,2-d]pyrimidine;

(±)-2,5-dimethyl-4-(tetrahydro-furan-3-yloxy)-7-(2,4,6-trimethyl-phenyl)-5H-pyrrolo-[3,2-d]pyrimidine;

2,5-methyl-4-(S)-(tetrahydro-furan-3-yloxy)-7-(2,4,6-trimethyl-phenyl)-5H-pyrrolo-[3,2-d]pyrimidine;

2,5-dimethyl-4-(1-propyl-butoxy)-7-(2,4,6-trimethyl-phenyl)-5H-pyrrolo[3,2-d]pyridine;

4-sec-butylsulfanyl-2,5-dimethyl-7-(2,4,6-trimethyl-phenyl)-5H-pyrrolo[3,2-d]pyrimidine;

4-(butyl-ethyl-amino)-2,6-dimethyl-8-(2,4,6-trimethyl-phenyl)-5,8-dihydro-6H-pyrido [2,3-d]pyrimidin-7-one;

8-(1-ethyl-propoxy)-6-methyl-4-(2,4,6-trimethyl-phenyl)-3,4-dihydro-1H-pyrido[2,3-b]pyrazin-2-one;

8-(1-ethyl-propoxy)-6-methyl-4-(2,4,6-trimethyl-phenyl)-1,2,3,4-tetrahydro-pyrido [2,3-b]pyrazine;

4-(1-ethyl-propoxy)-2-methyl-8-(2,4,6-trimethyl-phenyl)-quinoline;

5-(1-ethyl-propoxy)-7-methyl-1-(2,4,6-trimethyl-phenyl)-1 4-dihydro-2H-3-oxa-1,8-diaza-naphthalene, 5-(1-ethyl-propoxy)-7-methyl-1-(2,4,6-trimethyl-phenyl)-1,2-dihydro-3-oxa-1,8-diaza-naphthalen-4-one;

8-(1-ethyl-propoxy)-1,6-dimethyl-4-(2,4,6-trimethyl-phenyl)-1,2,3,4-tetrahydro-pyrido[2,3-b]pyrazine;

(1-ethyl-propyl)-[2-methyl-8-(2,4,6-trimethyl-phenyl)-quinolin-4-yl]-amine;

4-(butyl-ethyl-amino)-2,4,6-dimethyl-8-(2,6-dimethyl-4-bromo-phenyl)-5,8-dihydro-6H-pyrido[2,3-d]pyrimidin-7-one;

4-(butyl-ethyl-amino)-2-methyl-8-(2,6-dimethyl-4-bromo-phenyl)-5,8-dihydro6H-pyrido[2,3-d]pyrimidin-7-one;

4-(1-ethyl-propoxy)-2-methyl-8-(2,6-dimethyl-4-bromo-phenyl)-5,8-dihydro-6H-pyrido[2,3-d]pyrimidin-7-one;

(butyl-ethyl)-[2-methyl-8-(2,6-dimethyl-4-bromo-phenyl)-5,6,7,8-tetrahydro-pyrido[2,3-d]pyrimidin-4-yl]-amine;

(propyl-ethyl)-[2-methyl-8-(2,6-dimethyl-4-bromo-phenyl)-5,6,7,8-tetrahydro-pyrido[2,3-d]pyrimidin-4-yl]-amine;

(diethyl)-[2-methyl-8-(2,6-dimethyl-4-bromo-phenyl)-5,6,7,8-tetrahydro-pyrido [2,3-d]pyrimidin-4-yl)-amine;

(1-ethyl-propyl)-[2-methyl-8-(2,6-dimethyl-4-bromo-phenyl)-5,6,7,8-tetrahydro-pyrido[2,3-d]pyrimidin-4-yl]-amine;

(1-ethyl-propoxy)-2-methyl-8-(2,6-dimethyl-4-bromo-phenyl)-5,6,7,8-tetrahydro-pyrido[2,3-d]pyrimidine;

4-(butyl-ethyl-amino)-2-methyl-8-(2,4,6-trimethyl-phenyl)-5,8-dihydro-6H-pyrido[2,3-d]pyrimidin-7-one;

4-(-ethyl-propoxy)-2-methyl-8-(2,4,6-trimethyl-phenyl)-5,8-dihydro-6H-pyrido[2,3-d]pyrimidin-7-one;

(butyl-ethyl)-[2-methyl-8-(2,4,6-trimethyl-phenyl)-5,6,7,8-tetrahydro-pyrido[2,3-d]pyrimidin-4-yl]-amine;

(propyl-ethyl)-[2-methyl-8-(2,4,6-trimethyl-phenyl)-5,6,7,8-tetrahydro-pyrido[2,3-d]pyrimidin-4-yl]-amine;

(diethyl)-[2-methyl-8-(2,4,6-trimethyl-phenyl)-5,6,7,8-tetrahydro-pyrido[2,3-d]pyrimidin-4-yl]-amine;

(1-ethyl-propyl)-[2-methyl-8-(2,4,6-trimethyl-phenyl)-5,6,7,8-tetrahydro-pyrido[2,3-d]pyrimidin-4-yl]-amine;

(1-ethyl-propoxy)-2-methyl-8-(2,4,6-trimethyl-phenyl)-5,6,7,8-tetrahydro-pyrido[2,3-d]pyrimidine;

8-(1-ethyl-propoxy)-6-methyl-4-(2,6-dimethyl-4-bromo-phenyl)-3,4-dihydro-1H-pyrido [2,3-b]pyrazin-2-one;

8-(1-ethyl-propoxy)-6-methyl-4-(2,6-dimethyl-4-bromo-phenyl)-1,2,3,4-tetrahydro-pyrido[2,3-b]pyrazine;

4-(1-ethyl-propoxy)-2-methyl-8-(2,6-methyl-4-bromo-phenyl)-quinoline;

5-(1-ethyl-propoxy)-7-methyl-1-(2,6dimethyl-4-bromo-phenyl)-1,4-dihydro-2H-3-oxa-1,8-diaza-naphthalene;

5-(1-ethyl-propoxy)-7-methyl-1-(2,6-dimethyl-4-bromo-phenyl)-1,2-dihydro-3-oxa-1,8-diaza-naphthalen-4-one;

8-(1-ethyl-propoxy)-1,6-dimethyl-4-(2,6-dimethyl-4-bromo-phenyl)-1,2,3,4-tetrahydro-pyrido[2,3-b]pyrazine;

(1-ethyl-propyl)-[2-methyl-8-(2,6-dimethyl-4-bromo-phenyl)-quinolin-4-yl]-amine;

4-(butyl-ethyl-amino)-2,6-dimethyl-8-(2,6-dimethyl-4-chloro-phenyl)-5,8-dihydro-6H-pyrido[2,3-d]pyrimidin-7-one;

8-(1-ethyl-propoxy)-6-methyl-4-(2,6-dimethyl-4-chloro-phenyl)-3,4-dihydro-1H-pyrido[2,3-b]pyrazin-2-one;

8-(1-ethyl-propoxy)-6-methyl-4-(2,6-dimethyl-4-chloro-phenyl)-1,2,3,4-tetrahydro-pyrido[2,3-b]pyrazine;

4-(1-ethyl-propoxy)-2-methyl-8-(2,6-dimethyl-4-chloro-phenyl)-quinoline;

5-(1-ethyl-propoxy)-7-methyl-1-(2,6-dimethyl-4-chloro-phenyl)-1,4dihydro-2H-3-oxa-1,8-diaza-naphthalene;

5-(1-ethyl-propoxy)-7-methyl(-1-(2,6-dimethyl4-chloro-phenyl)-1,2-dihydro-3-oxa-1,8-diaza-naphthalen-4-one;

8-(1-ethyl-propoxy)-1,6-dimethyl-4-(2,6-dimethyl-4-chloro-phenyl)-1,2,3,4-tetrahydro-pyrido[2,3-b]pyrazine;

(1-ethyl-propyl)-[2-methyl-8-(2,6-dimethyl-4-chloro-phenyl)-quinolin-4-yl]-amine;

8-(1-hydroxymethyl-propoxy)-6-methyl-4-(2,4,6-trimethyl-phenyl)-3,4-dihydro-1H-pyrido[2,3-b]pyrazin-2-one;

8-(1-hydroxymethyl-propylamino)-6-methyl-4-(2,4,6-trimethyl-phenyl)-3,4-dihydro-1H-pyrido[2,3-b]pyrazin-2-one;

8-(1-ethyl-propylamino)-6-methyl-4-(2,4,6-trimethyl-phenyl)-3,4-dihydro-1H-pyrido[2,3-b]pyrazin-2-one;

8-diethylamino-6-methyl-4-(2,4,6-trimethyl-phenyl)-3,4-dihydro-1H-pyrido[2,3-b]pyrazin-2-one;

8-(ethyl-propyl-amino)-6-methyl-4-(2,4,6-trimethyl-phenyl)-3,4-dihydro-1H-pyrido[2,3-b]pyrazin-2-one;

8-(butyl-ethyl-amino)-6-methyl-4-(2,4,6-trimethyl-phenyl)-3,4-dihydro-1H-pyrido[2,3-b]pyrazin-2-one;

8-(1-hydroxymethyl-propoxy)-6-methyl-4-(2,4,6-trimethyl-phenyl)-1,2,3,4-tetrahydro-pyrido[2,3-b]pyrazine;

8-(1-hydroxymethyl-propylamino)-6-methyl-4-(2,4,6-trimethyl-phenyl)-1,2,3,4-tetrahydro-pyrido[2,3-b]pyrazine;

8-(1-ethyl-propylamino)-6-methyl-4-(2,4,6-trimethyl-phenyl)-1,2,3,4-tetrahydro-pyrido[2,3-b]pyrazine;

8-diethylamino-6-methyl-4-(2,4,6-trimethyl-phenyl)-1,2,3,4-tetrahydro-pyrido[2,3-b]pyrazine;

8-(ethyl-propyl-amino)-6-methyl-4-(2,4,6-trimethyl-phenyl)-1,2,3,4-tetrahydro-pyrido[2,3-b]pyrazine;

8-(butyl-ethyl-amino)-6-methyl-4-(2,4,6-trimethyl-phenyl)-1,2,3,4-tetrahydro-pyrido[2,3-b]pyrazine;

4-(1-hydroxymethyl-propoxy)-2-methyl-8-(2,4,6-trimethyl-phenyl)-quinoline;

4-(1-hydroxymethyl-propylamino)-2-methyl-8-(2,4,6-trimethyl-phenyl)-quinoline;

4-(1-ethyl-propylamino)-2-methyl-8-(2,4,6-trimethyl-phenyl)-quinoline;

4-diethylamino-2-methyl-8-(2,4,6-trimethyl-phenyl)-quinoline;

4-(ethyl-propyl-amino)-2-methyl-8-(2,4,6-trimethyl-phenyl)-quinoline;

4-(butyl-ethyl-amino)-2-methyl-8-(2,4,6-trimethyl-phenyl)-quinoline;

5-(1-hydroxymethyl-propoxy)-7-methyl-1-(2,4,6-trimethyl-phenyl)-1,4-dihydro-2H-3oxa-1,8diaza-naphthalene;

5-(1-hydroxymethyl-propylamino)-7-methyl-1-(2,4,6-trimethyl-phenyl)-1,4-dihydro-2H-3-oxa-1,8-diaza-naphthalene;

5-(1-ethyl-propylamino)-7-methyl-1-(2,4,6-trimethyl-phenyl)-1,4-dihydro-2H-3-oxa-1,8 diaza-naphthalene;

5-diethylamino-5-methyl-1-(2,4,6-trimethyl-phenyl)-1,4-dihydro-2H-3oxa-1,8-diaza-naphthalene;

5-(ethyl-propyl-amino)-7-methyl-1-(2,4,6-trimethyl-phenyl)-1,4-dihydro-2H-3-oxa-1,8-diaza-naphthalene;

8-(butyl-ethyl-amino)-6-methyl-4-(2,4,6-trimethyl-phenyl)-1,4dihydro-2H-3-oxa-1,8-diaza-naphthalene;

4-(2,4-dichlorophenyl)-5-methyl-2-[N-(1-(methoxymethyl)-1-(naphth-2-yl)methyl)-N-propylamino]thiazole;

oxalate of 4-(2,4-dichlorophenyl)-5-methyl-2-N-6-methoxyisoquinol-5yl)-N-propylamino]thiazole;

oxalate of 4-(2-chloro-4-methoxyphenyl)-5-methyl-2-[N-(6-methylisoquinol-5-yl)-N-propylamino]thiazole;

4-(2-chloro-4-methoxyphenyl)-5-methyl-2-[N-(1-methoxycarbonylmethylindol-5-yl)-N-propylamino]thiazole;

oxalate of 4-(2-chloro-4-methoxyphenyl)-5-methyl-2-[N-(6-methoxyisoquinol-5-yl)-N-propylamino]thiazole;

oxalate of 4-(2-chloro-4-methoxyphenyl)-5-methyl-2-[N-(6-chloroisoquinol-5-yl)-N-propylamino]thiazole;

oxalate of 4-(2-chloro-4-methoxyphenyl)-5-methyl-2-[N-(6-methoxyisoquinol-5yl)-N-propylamino]thiazole;

4-(2-chloro-4-methoxyphenyl)-5-methyl-2-[N-(1-methoxynaphth-2-yl)-N-propyl]thiazole;

oxalate of 4-(2-chloro4-trifluoromethylphenyl)-5-methyl-2-[N -6-methoxylsoquinol-5-yl)-N-propyl]thiazole;

chlorhydrate of 4-(2-chloro-4-methoxyphenyl)-5-methyl-2-[N-(2-ethoxynaphth-1-yl)-N-propylamino]thiazole, chlorhydrate of 4-(2-chloro-4-methoxyphenyl)-5-methyl-2[N-(2,3-dimethylnaphth-1-yl)-N-propylamino]thiazole;

chlorhydrate de 4-(2-chloro4-methoxyphenyl)-5-methyl-2-[N-(6-bromo-2-methoxynaphth-1-yl)-N-propylamino]thiazole;

chlorhydrate of 4-(2-chloro-4-methoxyphenyl)-5-methyl-2-[N-(2,6-dimethylnaphth-1-yl)-N-propylamino]thiazole;

chlorhydrate of 4-(2-chloro4-methoxyphenyl)-5-methyl-2-[N-(1-(methoxymethyl)-1-(naphth-2-yl)methyl)-N-propylamino]thiazole;

chlorhydrate of 4-(2-chloro-4-methoxyphenyl)-5-methyl-2-[N-(1-(cyclopropyl)-1-(naphth-2-yl)methyl)-N-propylamino]thiazole;

3-(2,4-dichlorophenyl)-5-methyl-7(N-propyl-N-cyclopropanemethylamino)-pyrazolo[2,3-a]pyrimidine;

3-(2,4-dichlorophenyl)-5-methyl-7-(N-allyl-N-cyclopropanemethylamino)-pyrazolo(2,3-a]pyrimidine;

2-methylthio-3-(2,4-dichlorophenyl)-5-methyl-7-(N,N-diallylamino)-pyrazolo[2,3-a]pyrimidine;

2-methylthio-3-(2,4-dichlorophenyl)-5-methyl-7-(N-butyl-N-cyclopropanemethylamino)pyrazolo[2,3-a]pyrimidine; 2-methylthio-3-(2,4-dichlorophenyl)-5-methyl-7-(N-propyl-N-cyclopopanemethyl-amino)pyrazolo[2,3-a]pyrimidine;

2-methyl-3-(4-chlorophenyl)-5-methyl-7-(N,N-dipropylamino)-pyrazolo[2,3-a]pyrimidine;

3-[6-(dimethylamino)-3-pyridinyl-2,5-dimethyl-N,N-dipropylpyrazolo[2,3-a]pyrimidin-7-amine;

3-[6-(dimethylamino)-4-methyl-3-pyridinyl]-2,5-dimethyl-N,N-dipropyl-pyrazolo[2,3-a]pyrimidine-7-amine;

3-(2,4-dimethoxyphenyl)-2,5-dimethyl-7-(N-propyl-N-methyloxyethylamino)-pyrazolo [2,3-a]pyrimidine;

7-(N-diethylamino)-2,5-dimethyl-3-(2-methyl-4-methoxyphenyl-[1,5-a]-pyrazolopyrimidine;

7-(N-(3-cyanopropyl)-N-propyl-2,5-dimethyl-3-(2,4-dimethylphenyl)-[1,5-a]pyrazolopyrimidine;

[3,6-dimethyl-2-(2,4,6-trimethyl-phenoxy)-pyridin-4-yl]-(1-ethyl-propyl)-amine;

[2-(4-chloro-2,6-dimethyl-phenoxy)-3,6-dimethyl-pyridin-4-yl]-(1-ethyl-propyl)-amine;

cyclopropylmethyl-[3-(2,4-dimethyl-phenyl)-2,5-dimethyl-pyrazolo[1,5-a]pyrimidin-7-yl]-propyl-amine;

cyclopropylmethyl-[3-(2-methyl-4-chloro-phenyl)-2,5-dimethyl-pyrazolo[1,5-a]pyrimidin-7-yl]-propyl-amine;

cyclopropylmethyl-[3-(2,4-di-chloro-phenyl)-2,5-dimethyl-pyrazolo[1,5-a]pyrimidin-7-yl]-propyl-amine;

[3-(2-methyl-4-chloro-phenyl)-2,5-dimethyl-pyrazolo[1,5-a]pyrimidin-7-yl]-di-propyl-amine;

[2,5-dimethyl-3-(2,4-dimethyl-phenyl)-pyrazolo[1,5-a]pyrimidin-7-yl]-(1-ethyl-propyl)-amine;

[2,5-dimethyl-3-(2,4-dichloro-phenyl)-pyrazolo[1,5-a]pyrimidin-7-yl]-(1ethyl-propyl)-amine; and 4-(1-Ethyl-propylamino)-6-methyl-2-(2,4,6-trimethyl-phenoxy)-nicotinic acid methyl ester.

4. The method of claim 1 wherein said condition is time zone change syndrome.

* * * * *